(12) United States Patent
Crawford

(10) Patent No.: US 9,017,411 B2
(45) Date of Patent: Apr. 28, 2015

(54) SPINAL SURGERY APPARATUS AND METHOD

(76) Inventor: Mark Crawford, Paducah, KY (US)

( * ) Notice: Subject to any disclaimer, the term of this patent is extended or adjusted under 35 U.S.C. 154(b) by 385 days.

(21) Appl. No.: 13/388,993

(22) PCT Filed: Nov. 5, 2010

(86) PCT No.: PCT/US2010/055531
§ 371 (c)(1), (2), (4) Date: Feb. 5, 2012

(87) PCT Pub. No.: WO2011/057032
PCT Pub. Date: May 12, 2011

(65) Prior Publication Data
US 2012/0271424 A1  Oct. 25, 2012

Related U.S. Application Data

(60) Provisional application No. 61/280,621, filed on Nov. 6, 2009.

(51) Int. Cl.
A61F 2/44 (2006.01)
A61B 17/17 (2006.01)
A61B 17/16 (2006.01)
A61B 17/88 (2006.01)
(Continued)

(52) U.S. Cl.
CPC ......... *A61B 17/1757* (2013.01); *A61B 17/1631* (2013.01); *A61B 17/1671* (2013.01); *A61B 17/86* (2013.01); *A61B 17/8875* (2013.01); *A61B 2019/462* (2013.01); *A61F 2/4455* (2013.01); *A61F 2/4611* (2013.01); *A61F 2/4684* (2013.01); *A61F 2002/3008* (2013.01); *A61F 2002/30495* (2013.01); *A61F 2002/30507* (2013.01); *A61F 2002/30616* (2013.01); *A61F 2002/4629* (2013.01); *A61F 2002/4677* (2013.01)

(58) Field of Classification Search
CPC ....... A61F 2/44; A61F 2/4455; A61F 2/4465; A61F 2/46; A61F 2/4611
USPC ............................................. 623/17.11–17.16
See application file for complete search history.

(56) References Cited

U.S. PATENT DOCUMENTS 5,031,203 A   7/1991  Trecha
5,334,205 A * 8/1994  Cain .............................. 606/96
(Continued)

FOREIGN PATENT DOCUMENTS

WO    WO 2006 020463    2/2006

OTHER PUBLICATIONS

ISR mailed Oct. 20, 2011.
(Continued)

*Primary Examiner* — Jerry Cumberledge
*Assistant Examiner* — Nicholas Plionis
(74) *Attorney, Agent, or Firm* — TannerPatent.com; Chris Tanner, Esq.

(57) ABSTRACT

A system for implementing an improved spinal fusion cage having a centrally-located fixation screwhole of diameter minimized to accommodate a variable-angle, intervertebral, cannulated fixation screw is disclosed. The system includes a rigid connection between the spinal fusion cage to the shaft of the fixation screw, and a variable angle drill targeting device for directing the fixation screw through the non-visually acquirable, centrally-located fixation screwhole without X-ray or other imaging guidance.

10 Claims, 42 Drawing Sheets

(51) Int. Cl.
*A61F 2/46* (2006.01)
*A61B 17/86* (2006.01)
*A61B 19/00* (2006.01)
*A61F 2/30* (2006.01)

(56) References Cited

U.S. PATENT DOCUMENTS

| | | | |
|---|---|---|---|
| 5,661,775 | A | 8/1997 | Cramer |
| 6,056,749 | A * | 5/2000 | Kuslich ............... 606/86 A |
| 6,210,415 | B1 * | 4/2001 | Bester ................. 606/96 |
| 7,118,577 | B2 | 10/2006 | Gitis |
| 8,388,627 | B2 | 3/2013 | Panchbhavi |
| 2003/0135279 | A1 | 7/2003 | Michelson |
| 2004/0082959 | A1 * | 4/2004 | Hayes et al. .......... 606/96 |
| 2005/0071004 | A1 * | 3/2005 | Re et al. ............. 623/13.11 |
| 2005/0165400 | A1 * | 7/2005 | Fernandez ............ 606/69 |
| 2006/0161154 | A1 * | 7/2006 | McAfee ............... 606/61 |
| 2006/0190090 | A1 * | 8/2006 | Plaskon ............... 623/22.36 |
| 2007/0067040 | A1 * | 3/2007 | Ferree ................. 623/17.16 |
| 2007/0083265 | A1 * | 4/2007 | Malone ............... 623/17.11 |
| 2007/0123884 | A1 * | 5/2007 | Abdou ................. 606/69 |
| 2007/0168036 | A1 | 7/2007 | Ainsworth et al. |
| 2007/0270879 | A1 * | 11/2007 | Isaza et al. ........... 606/104 |
| 2008/0033440 | A1 | 2/2008 | Moskowitz |
| 2008/0039857 | A1 * | 2/2008 | Giersch et al. ........ 606/96 |
| 2008/0255563 | A1 | 10/2008 | Farr |
| 2009/0062921 | A1 | 3/2009 | Michelson |
| 2009/0240253 | A1 * | 9/2009 | Murray ................ 606/96 |
| 2010/0145391 | A1 * | 6/2010 | Kleiner ................ 606/279 |
| 2011/0077685 | A1 * | 3/2011 | Carls et al. ........... 606/247 |
| 2011/0077747 | A1 * | 3/2011 | Geller ................. 623/23.15 |
| 2011/0288600 | A1 | 11/2011 | Ritchey |
| 2012/0035468 | A1 | 2/2012 | Ritchey |

OTHER PUBLICATIONS

Extended European Search Report of Nov. 15, 2013.

* cited by examiner

SPINAL SURGERY APPARATUS AND METHOD

CROSS-REFERENCE TO RELATED APPLICATIONS

This international application claims priority to International Application No. PCT/US2010/055531, filed on Nov. 5, 2010, which in turn claims priority to U.S. Provisional Application No. 61/280,621, filed on Nov. 6, 2009, where the entire contents of both applications are incorporated by reference herein.

FIELD OF THE INVENTION

This invention relates generally to a surgical apparatus, and a procedure and method for using that apparatus.

BACKGROUND OF THE INVENTION

A spinal fusion is a surgical procedure that promotes two back bones, or vertebrae, growing together into one bone. FIG. 1 models the front or anteroposterior view of two such vertebrae L5 (104) and S1 (108) separated by a disc 112. FIG. 2 models the side or lateral view of the same. As shown in FIG. 3, in the course of the spinal fusion, a fusion cage 304 is at times required.

The fusion cage 304 is a medical implant that is used to replace the removed disc between two vertebrae or to replace one or more vertebrae and their adjacent disc. Fenestrations 308 in these cages are usually filled with a bone grafting material that promotes a bony fusion between the bone above the cage and the bone below the cage. A screwhole 312 is usually provided in the front of the cage to accommodate an insertion handle used in positioning the cage into the disc space. Fusion cages are supplied in various sizes to fit the space between the bones being fused. As shown in FIG. 4, a trial cage 404 can be used to select the desired size fusion cage to fit into the disc space.

In some situations it is desirable to mechanically fix together the bones above and below the cage in order to limit movement between the bones and cages, thus promoting successful fusions and preventing cage displacement. This fixation can be accomplished as shown in FIG. 5 by passing a guide pin 504 into the bone on the near side of the cage, through a fenestration 308 in the interior of the fusion cage 304, and then into the bone on the far side of the cage. A fixation screw 508 can then be inserted over the guide pin 504 after which the guide pin is then removed. As FIG. 6 illustrates, the cage fenestration 308 cannot be visually acquired with the cage 304 in place in the disc. The trajectory of the guide pin 504, starting from the visually acquired guide pin entry point 604, must instead be directed with the use of x-rays.

In order to visualize the location of the cage fenestration 308 (FIG. 5) through which a fixation screw 508 is to pass, metal markers are placed in the wall of the fusion cage 304 that are immediately adjacent to this fenestration 308.

FIG. 7 illustrates the front view of the spine shown in FIG. 6 as it would appear on an x-ray. The L5 backbone 104 and S1 backbone 108 would be seen. Since the fusion cage 304 and the remaining disc 112 are invisible on x-ray, an empty space would appear in their place. Because, like bone, metal is visible on x-ray, metal markers in the walls of the cage fenestration 308 would be visible. The surgeon would be able to acquire the right side wall marker 704 and the left side wall marker 708.

FIG. 8 illustrates the side view of the spine pictured in FIG. 6 as it would appear on an x-ray. The L5 backbone 104 and the S1 backbone 108 would be visible. Again, an empty space would appear in the place of fusion cage 304 and any remaining disc 112. On the x-ray, the surgeon would be able to acquire the additional front wall marker 804 and the rear wall marker 808. As depicted in FIG. 8, these markers can be made in a different shape in order to distinguish them from the side wall markers 704 and 708 shown in FIG. 7.

Being metallic, the guide pin 504 can also be seen on an x-ray. Using the front x-ray view exemplified by that shown in FIG. 7, a surgeon would direct the guide pin 504 between the right side wall marker 704 and the left side wall marker 708. Using the side x-ray view FIG. 8, the surgeon simultaneously directs the guide pin 504 between the front wall marker 804 and the rear wall marker 808.

The surgeon would thus be assured that s/he has passed the guide pin 504 through the L5 backbone 104, through the cage fenestration 308 in the fusion cage 304, and into the S1 backbone 108. The surgeon can then insert the fixation screw 508 down over the guide pin 504 as shown in FIG. 7 and FIG. 8. The guide pin 504 would then be removed, leaving the fixation screw 508 in position passing through the cage fenestration 308 in the fusion cage 304.

Unfortunately, due to the difficulty in directing a guide pin 504 through a screwhole fenestration 308 in a fusion cage 304 using x-rays, the screwhole fenestration 308 must be significantly larger than the fixation screw 508. As a result, it is possible for the fusion cage 304 to partially displace out of the disc 112. This displacement can then result in excessive movement between the L5 backbone 104 and the S1 backbone 108, resulting in a failure of the spinal fusion. As shown in FIG. 5, a large screwhole fenestration 308 leaves any remaining fenestrations in the fusion cage 304 to be small. This results in most of the bone grafting material being placed in the screwhole fenestration 308, which is unwanted.

Further, passage of the fixation screw 508 through the screwhole fenestration 308 can disturb this bone grafting material and adversely impact a successful spinal fusion. It is therefore desirable to make the screwhole fenestration 308 as small as possible in order to prevent cage migration, and to allow the remaining fenestrations to be as large as possible and to carry the majority of the bone grafting material.

SUMMARY OF THE INVENTION

It is an object of the present invention to provide an apparatus and method for performing specific types of spinal surgeries. The apparatus and method assist in permanently locating a fusion cage within a spine. It is an additional object of the present invention to make the surgical procedures easier and safer to perform. These and other objects and advantages of the invention will become readily apparent as the following description is read in conjunction with the accompanying drawings.

DETAILED DESCRIPTION OF THE PREFERRED EMBODIMENTS

Before explaining the disclosed embodiment of the present invention in detail it is to be understood that the invention is not limited in its application to the details of the particular arrangement shown, since the invention is capable of other embodiments. Also, the terminology used herein is for the purpose of description and not of limitation.

Figure 8:
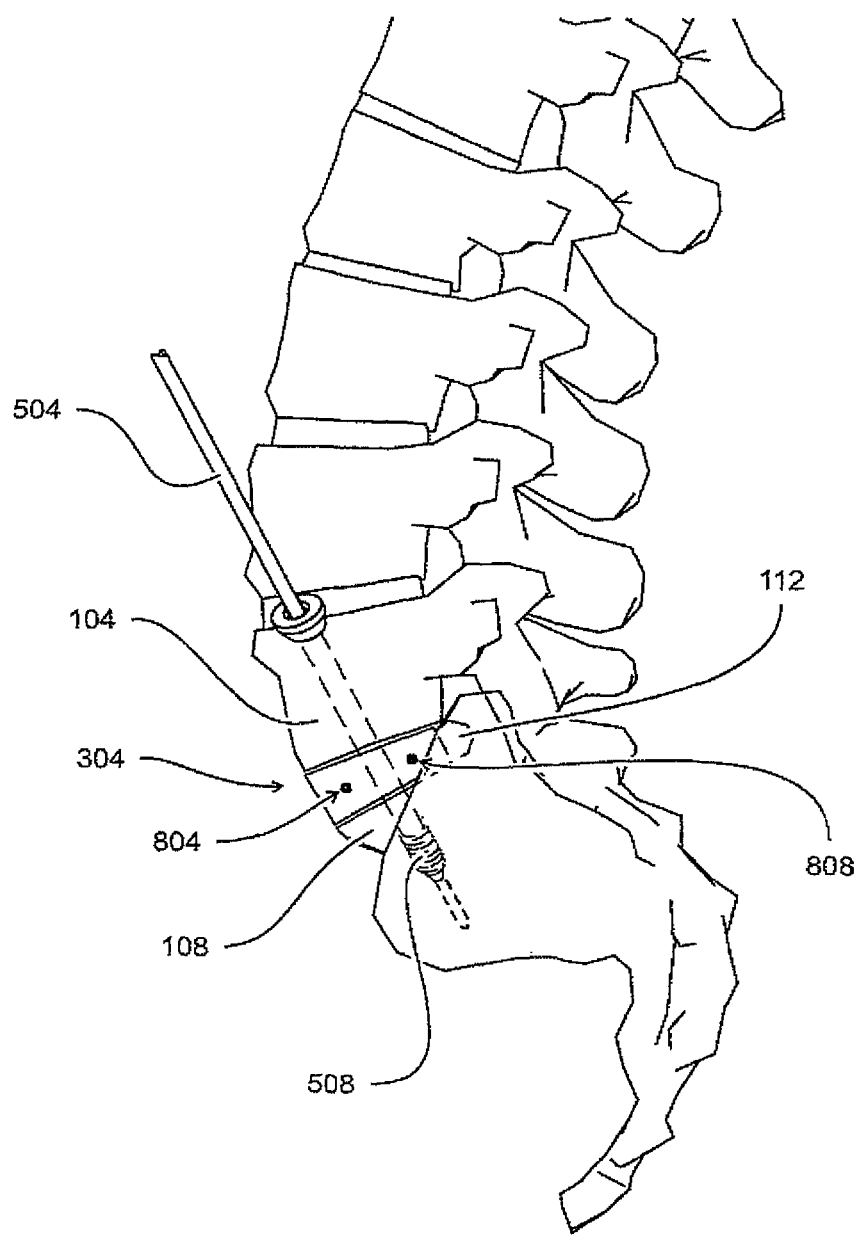
Figure 9A:
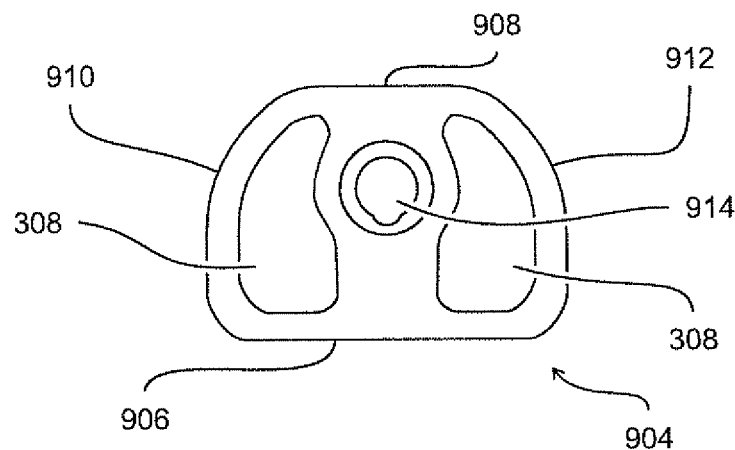
FIGS. 9A, 9B, 9C, and 9D show, respectively, plan, front, right-side, and cross-sectional right-side views of a modified fusion cage.
Figure 10A:
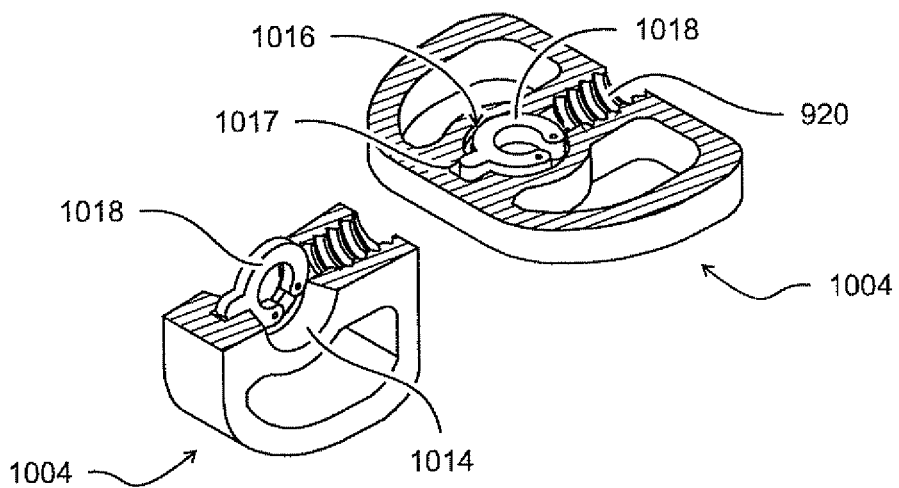
FIG. 10A shows a plan view and cross-sectional right side view of a second version of a modified fusion cage.
Figure 11A:
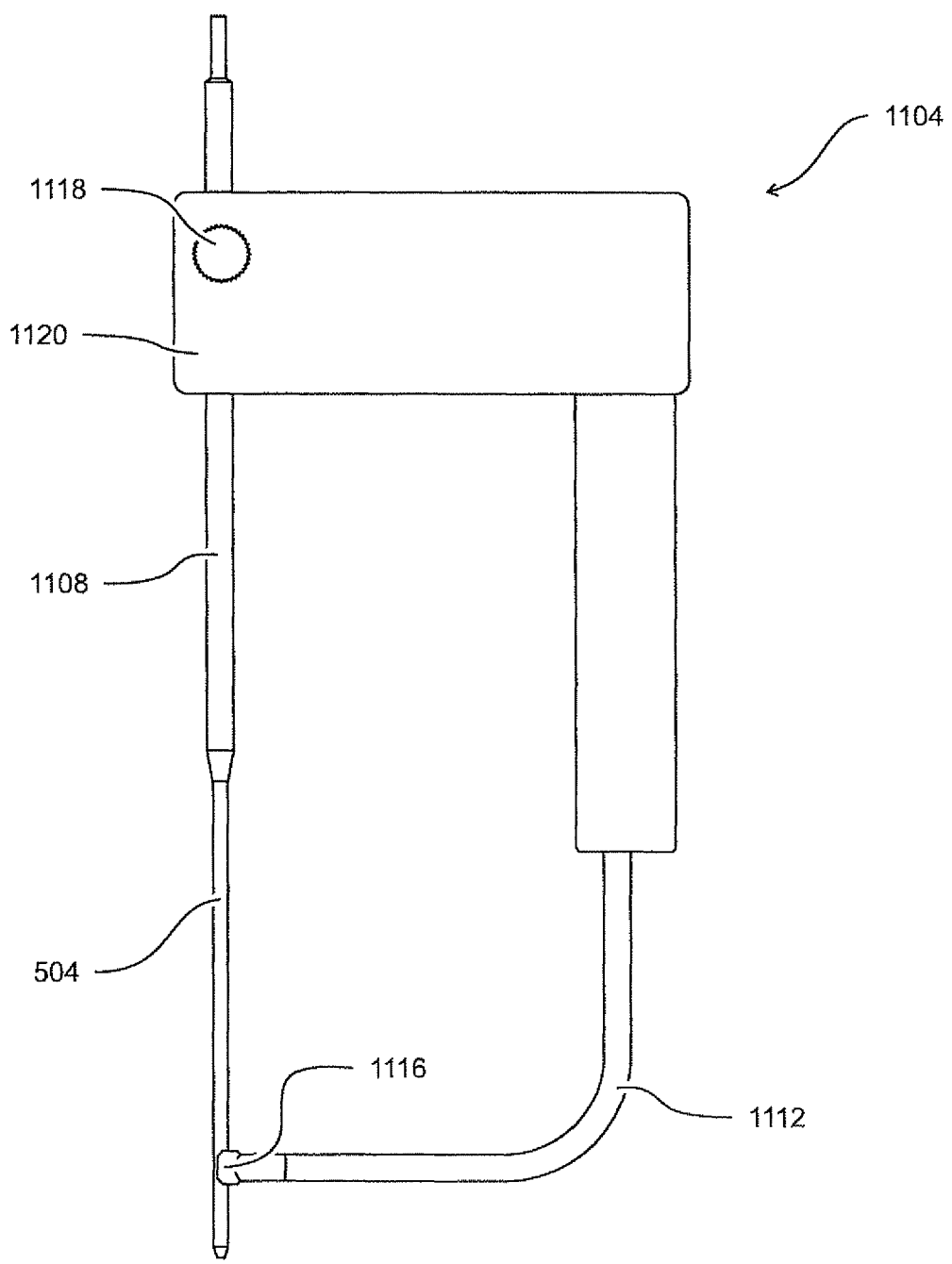
FIG. 11A shows a rigid drill targeting device.
Figure 12A:
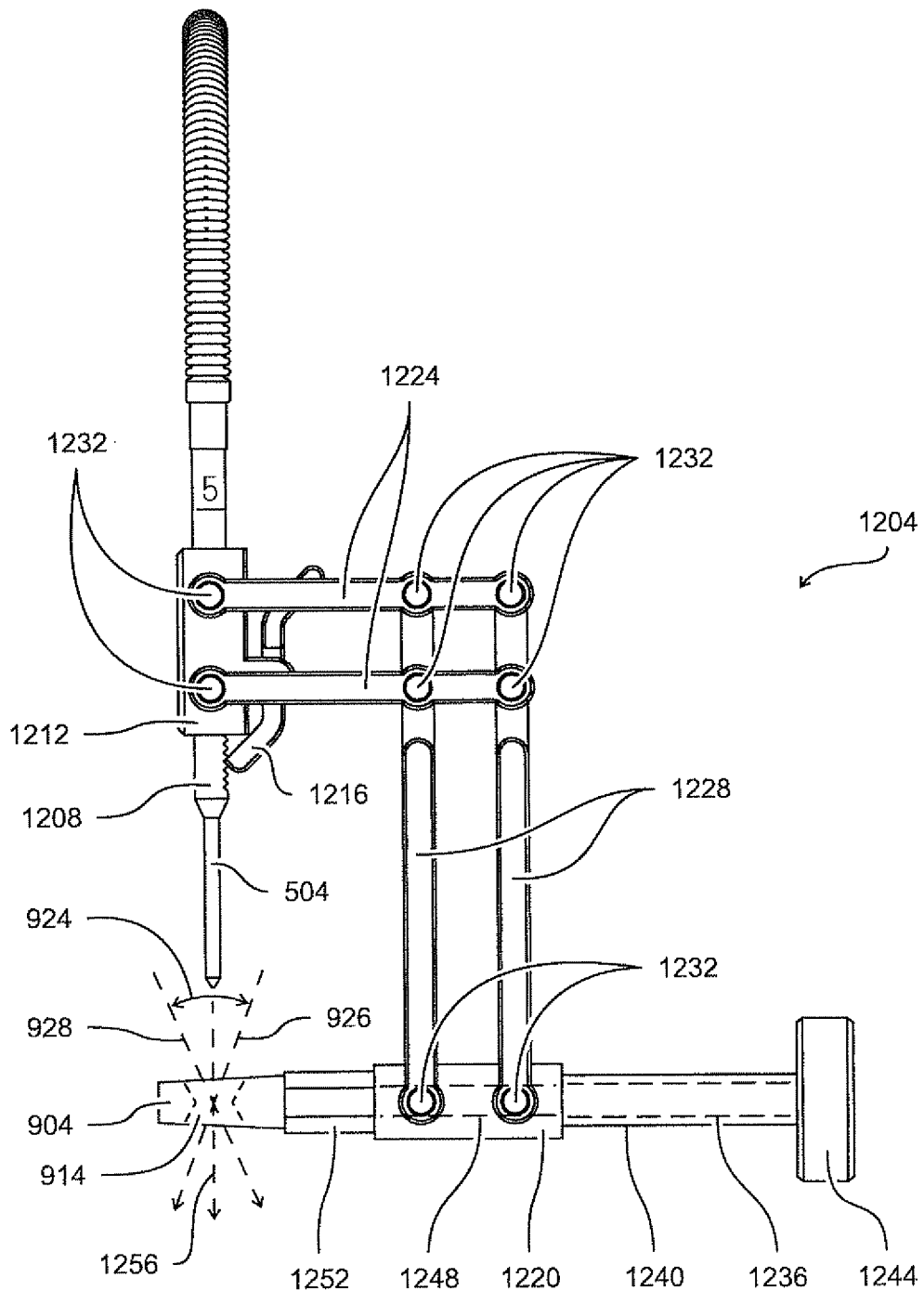
FIG. 12A shows a left side view of an articulating drill targeting device.

The embodiments disclosed herein involve the use of a rigid drill targeting device 1104 such as that shown in FIG. 11A or an articulating drill targeting device 1204 such as shown in FIG. 12A combined with a modified fusion cage 904 FIG. 9A, or with a modified fusion cage 1004 FIG. 10A. As noted earlier, a fusion cage is a medical implant that is to be permanently installed within a human spine. The targeting devices disclosed herein and other elements are combined to direct a guide pin 504 (e.g. FIG. 8) along the desired trajectory for placing a screw through the bone on the near side of the modified fusion cage 904 or modified fusion cage 1004, through a fixation screwhole 914 in modified fusion cage 904 (e.g. FIG. 9A) or a fixation screwhole 1014 in a modified fusion cage 1004 (e.g. FIG. 10A), and into the bone on the far side of the modified fusion cage 904 or modified fusion cage 1004. The drawings herein illustrating the various embodiments generally show to the L5 and S1 vertebrae. However, it is to be noted that the L5 and S1 vertebrae are but examples, for illustration only. The embodiments discussed herein can also be used on other combinations of vertebrae besides those explicitly shown in the drawings.

A first advantage is that X-ray guidance of the guide pin 504 is not required. The improved accuracy of insertion of guide pin 504 allows the fixation screwhole 914 or fixation screwhole 1014 to be made in a diameter that is near or the same as that of the fixation screw 508.

A second advantage is that the risk of cage migration is eliminated. The remaining cage fenestrations can be made as large as possible and will contain all of the bone grafting material. There is no bone grafting material to be disturbed by the insertion of the fixation screw 508.

FIG. 9A shows the plan view of a modified fusion cage 904 having a front 906, back 908, right side 910, and left side 912. A centrally-located fixation screwhole 914 accommodates passage of a guide pin 504 followed by a fixation screw 508 as was illustrated at least within FIGS. 7 and 8. As shown in FIG. 9A, additional fenestrations 308 accommodate bone grafting material.

Figure 9B:
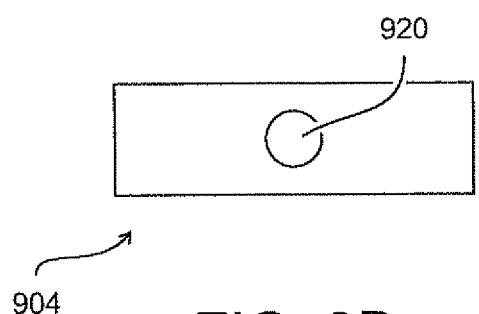
Figure 9C:
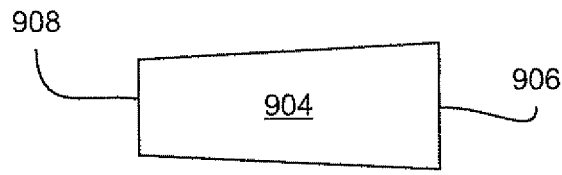
Figure 9D:
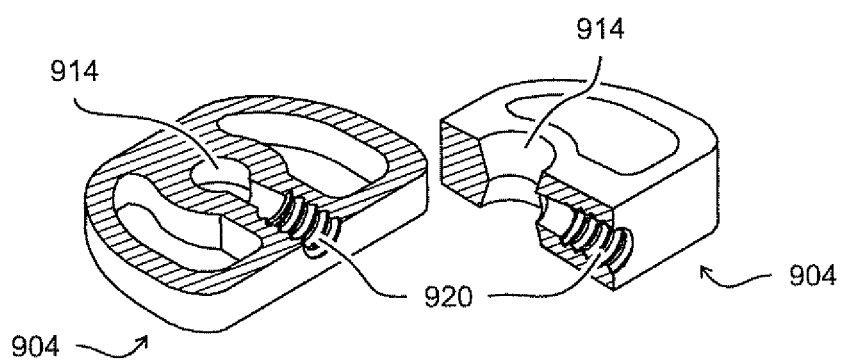

FIG. 9B shows the front view of the modified fusion cage 904 incorporating a utility screwhole 920 which connects with the fixation screwhole 914. FIG. 9C shows the right side view of the modified fusion cage 904 with the taller front 906 and shorter back 908 which fit the tapered shape of disc 112 that the modified fusion cage 904 replaces. FIG. 9D shows the cross-sectional right side view of the modified fusion cage 904 illustrating an hourglass shape of the fixation screwhole 914. Also shown is the connecting utility screwhole 920.

Figure 9E:
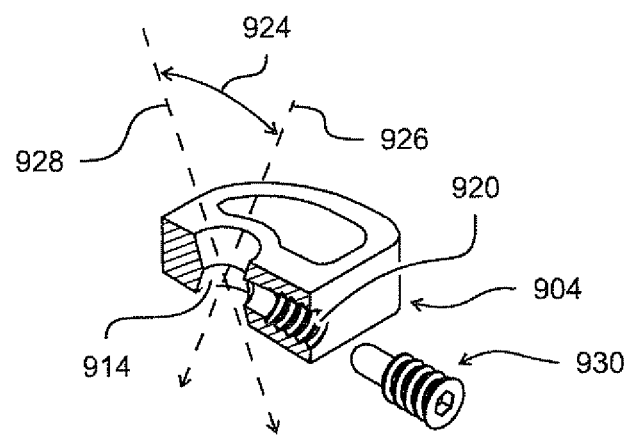
FIG. 9E shows the modified fusion cage of FIGS. 9A-9D including front and rear trajectories.

FIG. 9E shows how this hourglass shape is necessary if the fixation screwhole 914 is to be made the smallest diameter possible yet still accommodate a fixation screw 508 being inserted along a trajectory which can vary through are 924 from a maximum front trajectory 926 to a maximum rear trajectory 928.

Figure 9F:
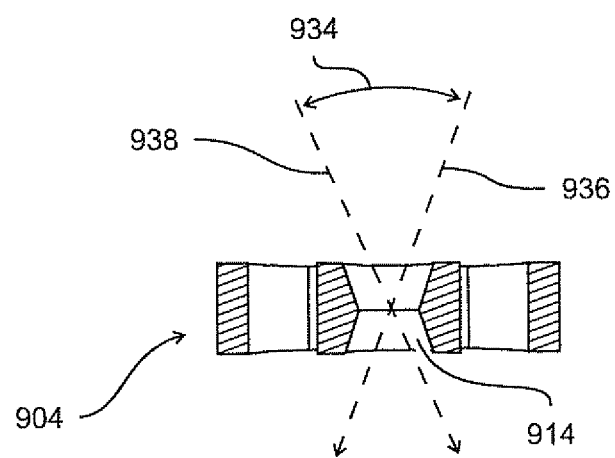
FIG. 9F shows the modified fusion cage of FIGS. 9A-9E including right and left trajectories.

Also illustrated within FIG. 9E is how the connecting utility screwhole 920 can accommodate the insertion of a locking screw 930 which can engage the fixation screw 508 and prevent it from subsequently migrating in or backing out of the fixation screwhole 914. In FIG. 9F, a cross-sectional front view of the modified fusion cage 904 shows how this same hourglass shape keeps the diameter of the fixation screwhole 914 to a minimum while accommodating a fixation screw 508 being inserted along a trajectory which can vary from a maximum left trajectory 936, through an arc 934, to a maximum right trajectory 938.

FIG. 10A shows a plan view and cross-sectional right side view of a second version of a modified fusion cage 1004 having the same features as the modified fusion cage 904, except for a further modification of fixation screwhole 914 resulting in the fixation screwhole 1014. This fixation screwhole 1014 includes a bearing or snap ring recess 1016 which accommodates a tilting bearing or snap ring 1018. The bearing or snap ring recess 1016 may incorporate an anti-spin recess 1017.

Figure 10B:
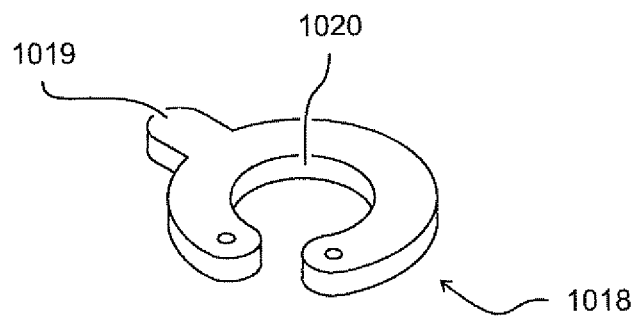
FIG. 10B shows a snap ring incorporating an anti-spin tab which fits into the anti-spin recess within the modified fusion cage of FIG. 10A.

FIG. 10B shows the snap ring 1018 incorporating an anti-spin tab 1019 which fits into the anti-spin recess 1017 located at the back of the bearing or snap ring recess 1016. The anti-spin recess is sufficiently large to allow the bearing or snap ring 1018 to tilt in the bearing or snap ring recess 1016, but small enough to prevent the bearing or snap ring 1018 spinning while fixation screw 508 is being inserted. The bearing or snap ring 1018 incorporates a central screwhole 1020 which is the same diameter as the fixation screw 508.

This same anti-spin feature maybe accomplished by making the bearing or snap ring recess 1016 non-circular in shape and making the bearing or snap ring 1018 have a matching non-circular outer shape.

While the hourglass shape of the fixation screwhole 914 in the modified fusion cage 904 reduces the diameter of the fixation screwhole 914 to a minimum, screw passage from a variety of angles as described at least within FIGS. 9E and 9F results in the minimum diameter at the waist of the hourglass-shaped fixation screwhole 914 still being slightly larger than the diameter of the fixation screw 508.

Undesired residual movement between the modified fusion cage 904 and the fixation screw 508 can be further reduced or eliminated by the locking screw 930. FIGS. 10C, 10D, 10E, and 10F illustrate how use of the tilting bearing or snap ring 1018 in the modified fusion cage 1004 achieves a fixation screwhole 1014 having a minimum diameter exactly matching the diameter of the fixation screw 508.

Figure 10C:
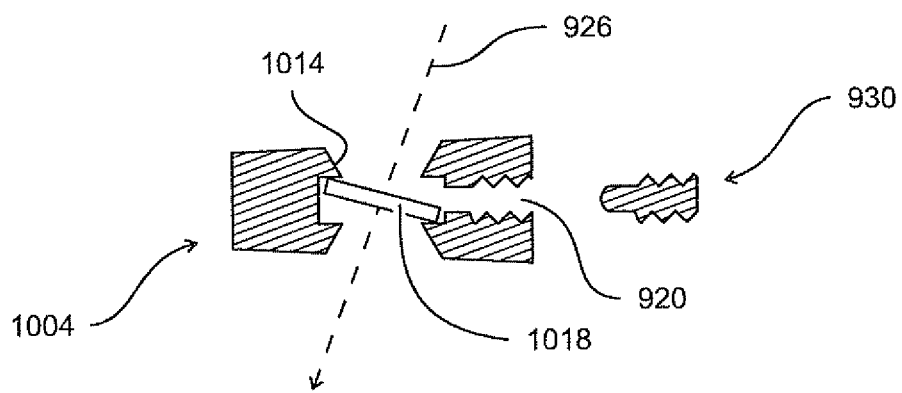
FIGS. 10C, 10D, 10E, and 10F illustrate a snap ring within the modified fusion cage of FIGS. 10A-10B.

FIG. 10C shows a cross-sectional right side view of the modified fusion cage 1004. The fixation screw 508 is being inserted along the maximum front trajectory 926. As the fixation screw 508 starts to thread itself through the central screwhole 1020 in the bearing or snap ring 1018, the bearing or snap ring 1018 will tilt to the front until it becomes perpendicular to the fixation screw 508.

Since the inner diameter of the bearing or snap ring 1018 matches the outer diameter of the fixation screw 508, there is no side-to-side movement possible between the two. Further, since the outer dimension of the tilting bearing or snap ring 1018 matches the inner dimension of the bearing or snap ring recess 1016, there is no side-to-side movement possible between these two either. The combined result ensures that no side-to-side movement is possible between the fixation screw 508 and the modified fusion cage 1004. As in the modified fusion cage 904, the locking screw 930 can then be inserted into the utility screwhole 920 to engage the fixation screw 508 and prevent its migrating in or backing out of the fixation screwhole 1014.

Figure 10D:
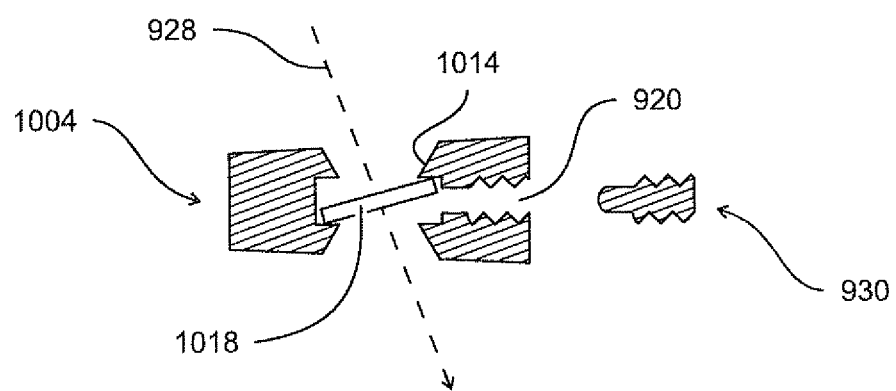
Figure 10E:
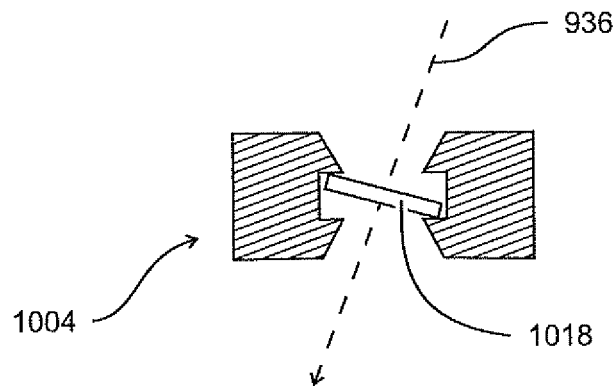
Figure 10F:
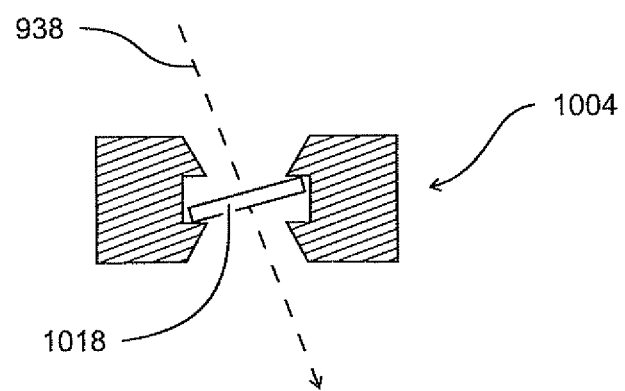

FIG. 10D shows the tilting bearing or snap ring 1018 tilted to the back accommodating insertion of a fixation screw 508 along the maximum back trajectory 928. Similarly, the cross-sectional front views at least within FIGS. 10E and 10F illustrate how the tilting bearing or snap ring 1018 can tilt respectively left accommodating the maximum left trajectory 936 or right accommodating the maximum right trajectory 938 for insertion of the fixation screw 508.

The tilting snap ring 1018 can be made with the diameter of the central hole 1020 (e.g. FIG. 10B) slightly smaller than the outer diameter of the fixation screw 508 and with the outer dimension of the snap ring 1018 similarly smaller than the inner dimension of the bearing or snap ring recess 1016. As the fixation screw 508 advances into the tilting snap ring 1018, the central hole 1020 will expand to the outer dimension of the fixation screw 508. The outer dimension of the snap ring 1018 will similarly expand to the inner dimension of the bearing or snap ring recess 1016. When the fixation screw 508 is in its final position, it can still be gripped tightly enough by the expanded snap ring 1018 to make the locking screw 930 unnecessary.

Figure 1:
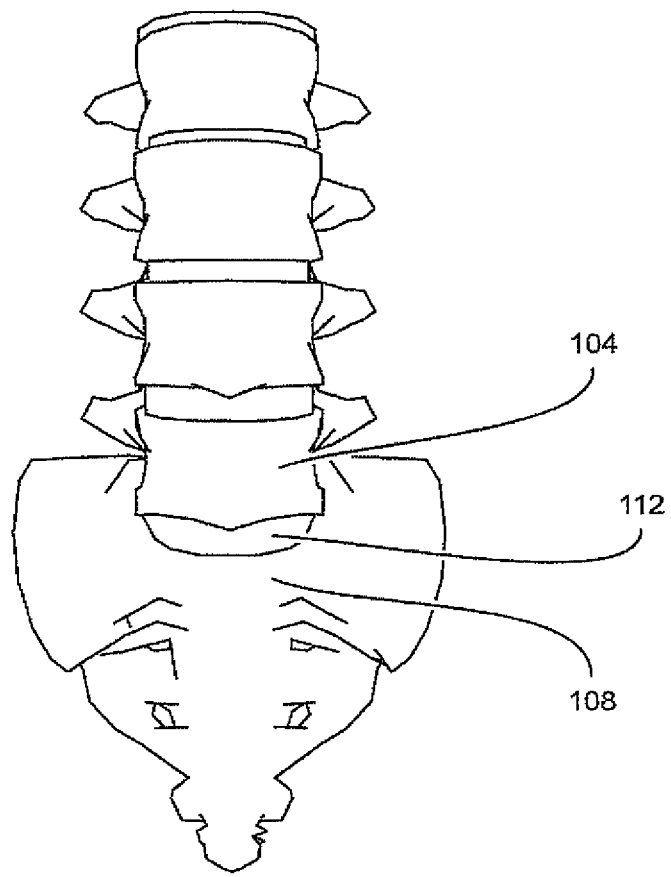
FIGS. 1 and 2 show front and side views, respectively, of two vertebrae.
Figure 2:
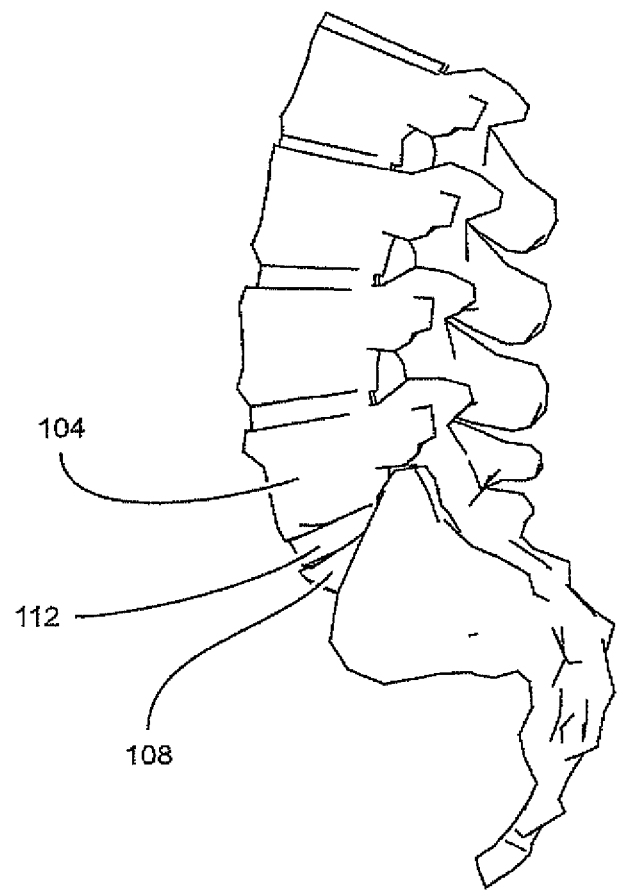
Figure 3:
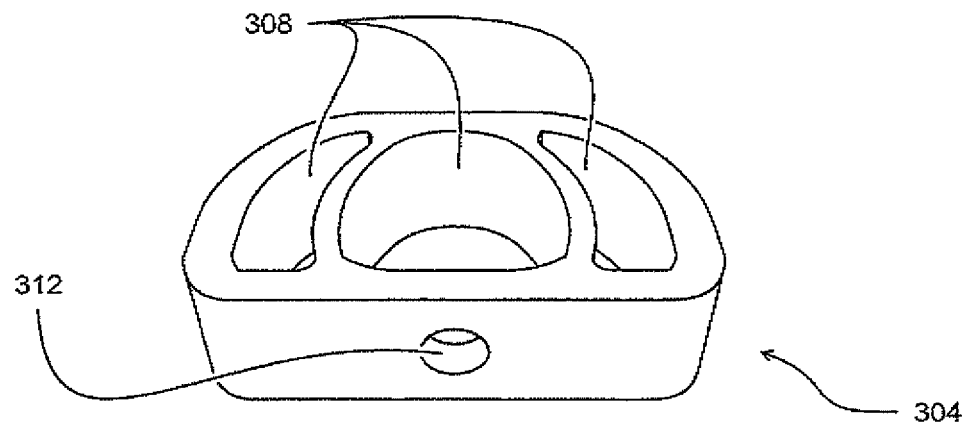
FIG. 3 shows an example fusion cage.
Figure 4:
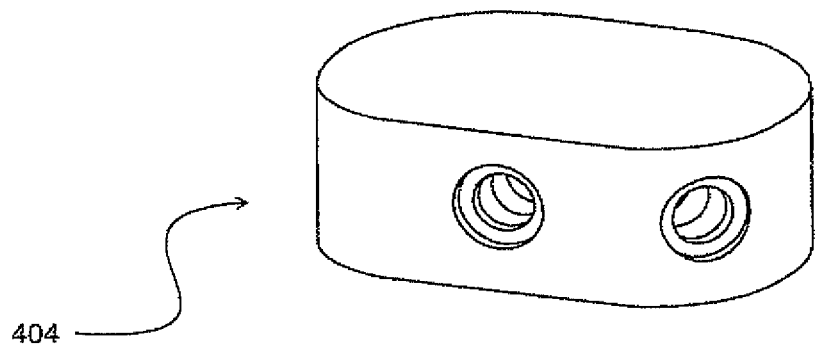
FIG. 4 shows an example trial cage.
Figure 5:
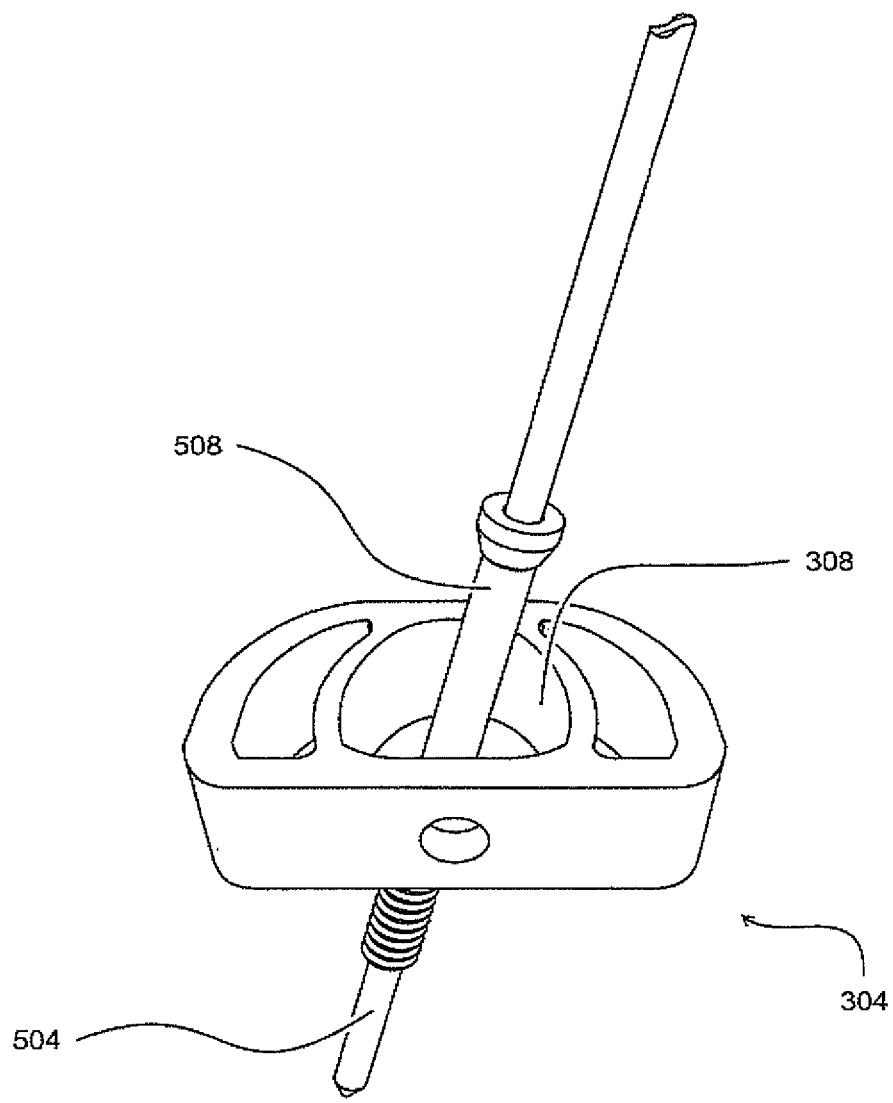
FIG. 5 shows an example guide pin and fixation screw within a fusion cage such as that shown in FIG. 3.

As shown in FIG. 5, insertion of a guide pin 504 through a large fenestration 308 using x-ray guidance can be challenging for the surgeon. Bringing an x-ray machine into the operative field requires the surgeon and his assistants to move out of the way while still trying to hold retractors and sharp instruments, such as guide pin 504, in position.

Figure 7:
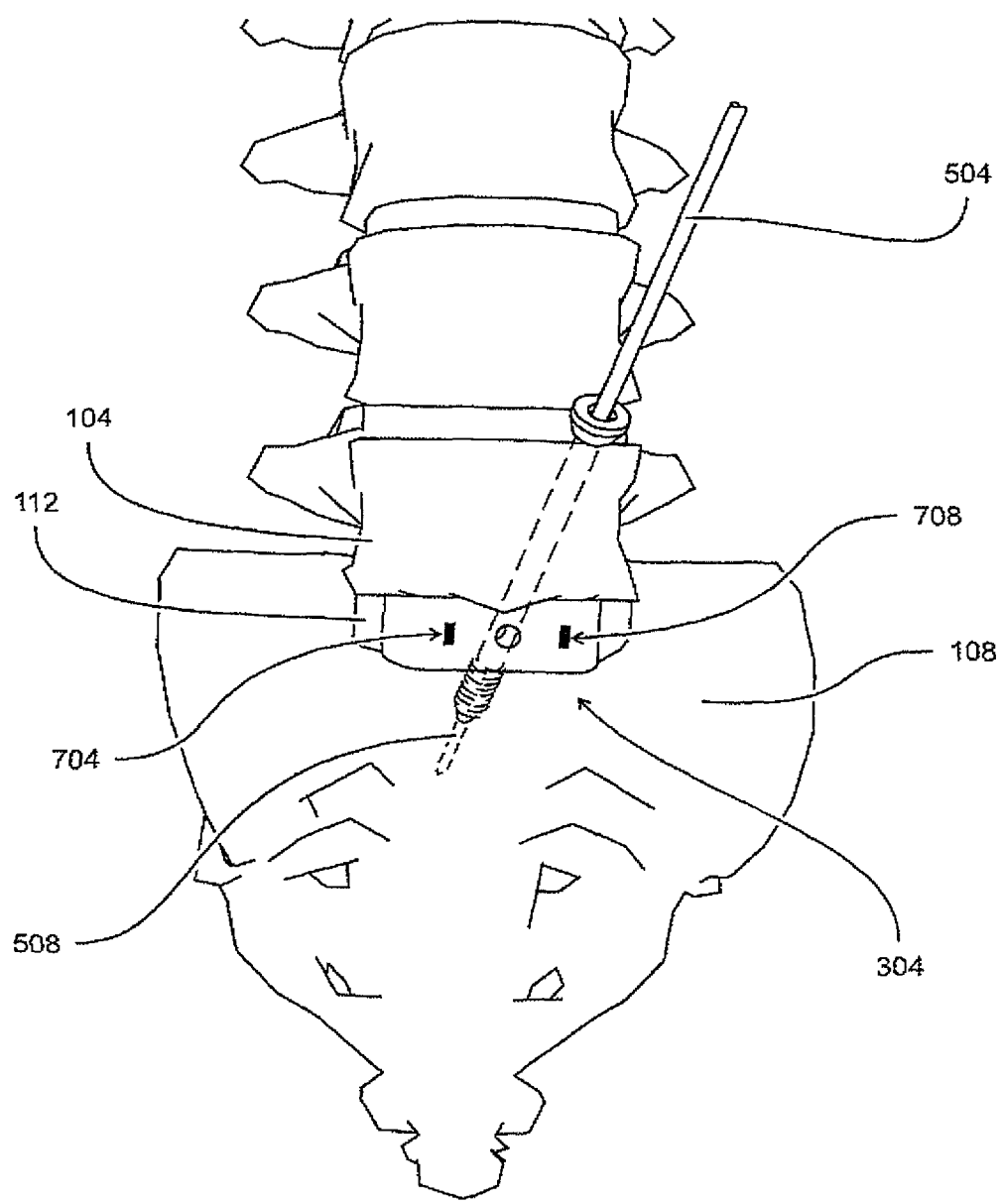
FIGS. 7 and 8 show the front and side views of the spine shown in FIG. 6.

As shown in FIG. 7, excellent hand-eye coordination is required for the surgeon to look at the relative position of the fusion cage 304, as denoted by the right side marker 704 and left side marker 708, and the guide pin 504 on the front x-ray view of the spine. The trajectory of the guide pin 504 in this side-to-side direction must be adjusted accordingly. The surgeon must then maintain the guide pin 504 in this exact position while the x-ray machine is re-positioned to expose the side view of the spine as shown in FIG. 8. Additional movement of surgeon and assistants maybe required to accommodate this repositioning of the x-ray machine. The surgeon must again rely on good hand-eye coordination while he looks at the side x-ray view of the spine and adjusts the trajectory of the guide pin 504 in this front-to-back direction before advancing the guide pin 504 into the backbone 104.

The surgeon then stops advancing the guide pin 504 and repeats the front and side x-rays and makes further adjustments to the trajectory. These further adjustments can be difficult because the guide pin 504 must be pulled back almost out of the backbone 104 before it can be re-directed. When then advanced in the corrected direction, the guide pin 504 may deflect back down the previous mis-aligned drill path. The guide pin 504 may then have to be completely removed from the back bone 104 and a new entry site for guide pin insertion selected. The entire previously described guide pin insertion process must then be started all over again.

While the placement depicted in FIG. 5 of a guide pin 504 through a large fenestration 308 in fusion cage 304 using the described x-ray guidance method is challenging, it is still possible in the hands of a sufficiently skilled surgeon. Conversely, the placement of a guide pin 504 through a minimal diameter fenestration, such as the fixation screwhole 914 in the modified fusion cage 904 or the fixation screwhole 1014 in modified fusion cage 1004, using the described x-ray guidance method, is sufficiently difficult as to be impractical. Consequently, in order to achieve the benefits of the tight fit between fixation screw 508 and modified fusion cage 904 or modified fusion cage 1004, an alternative guidance method for placement of the guide pin 504 is required.

As shown in FIG. 11A, a rigid drill targeting device 1104 consists of a small sliding pipe or drill guide 1108 mounted in a guide body 1120. A drill arm 1112 connects a semi-circular drill target 1116 to the guide body 1120. The sliding drill guide 1108 is secured by a thumbscrew 1118. The drill guide 1108 directs the guide pin 504 precisely through the notch in the drill target 1116 on the opposite end of the drill arm 1112.

Figure 11B:
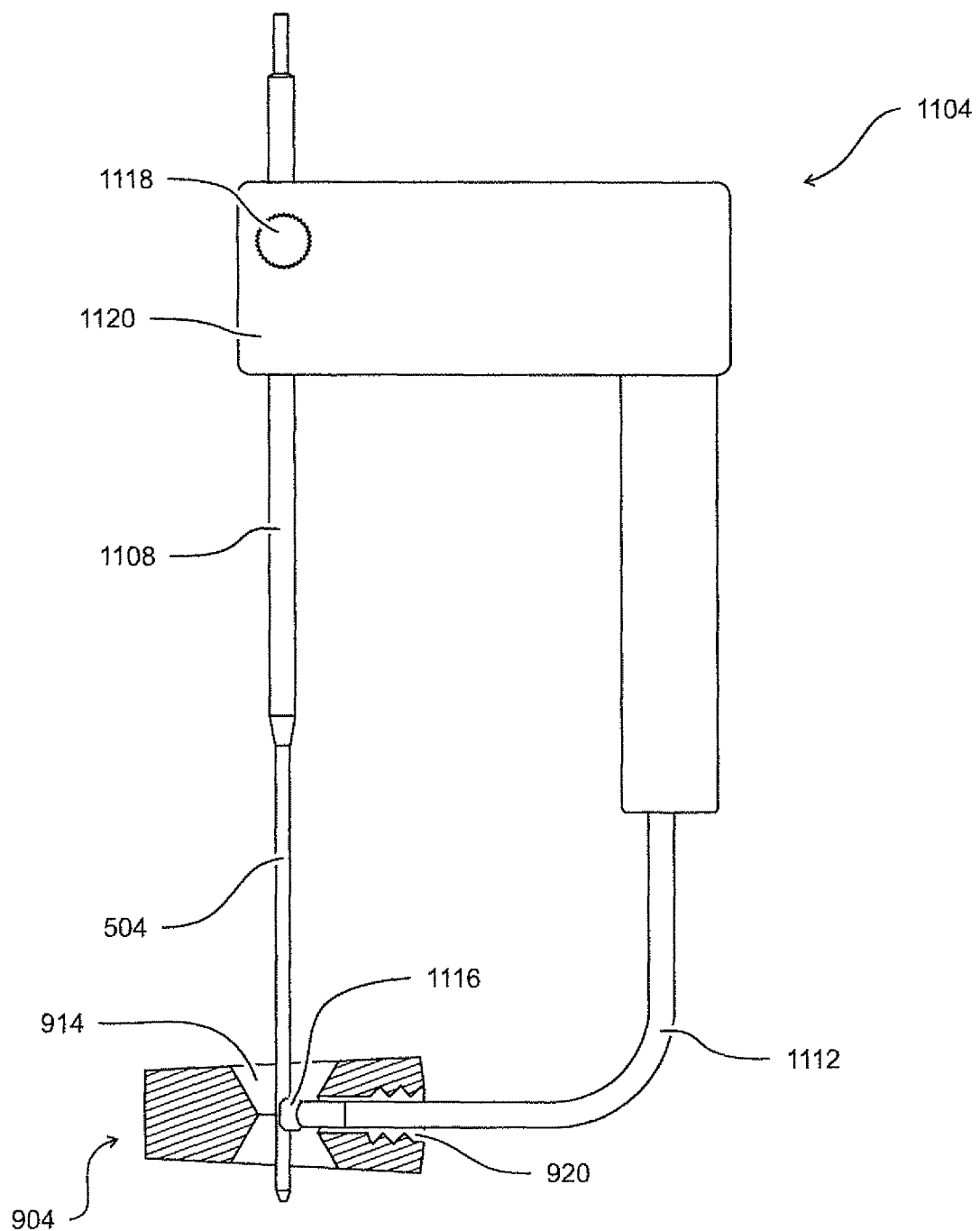
FIGS. 11B and 11C show a drill target inserted through a utility screwhole in a modified fusion cage.
Figure 11C:
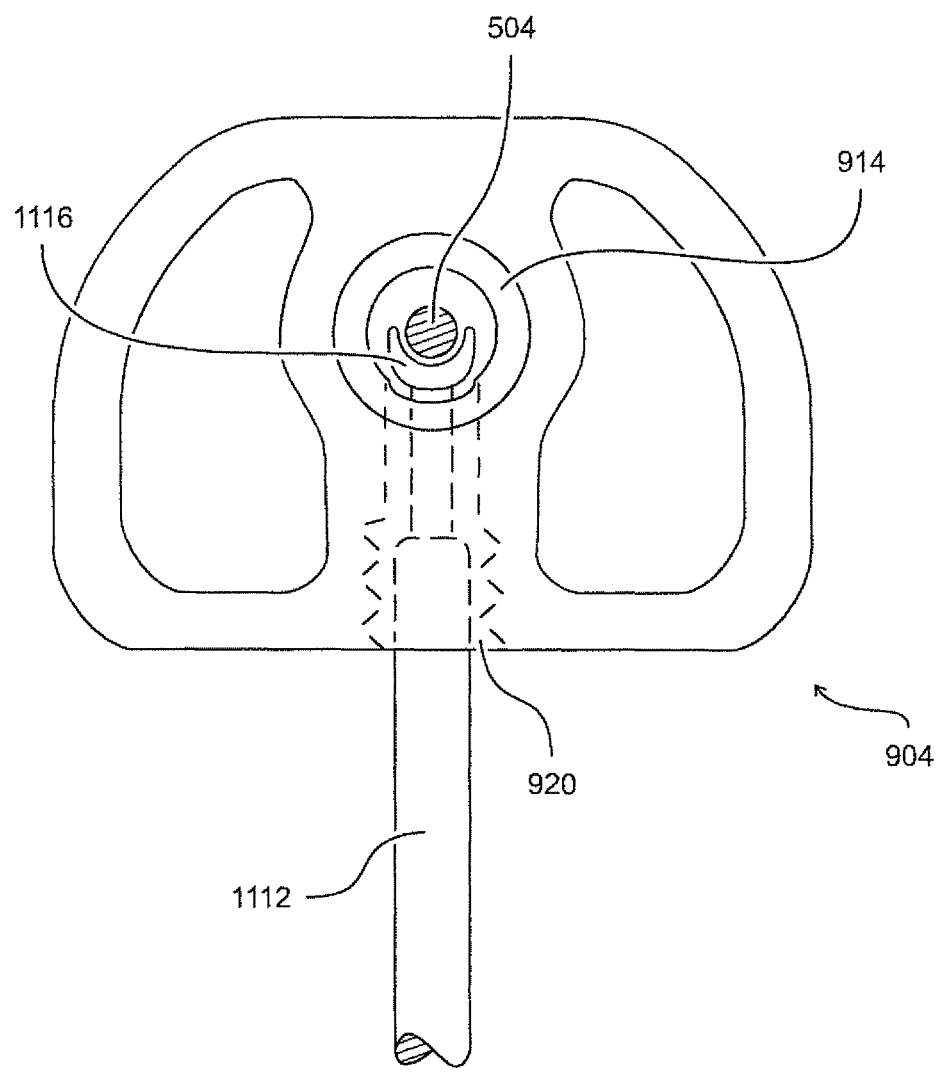

FIGS. 11B and 11C show how the drill target 1116 can be inserted through the utility screwhole 920 in the modified fusion cage 904 to engage the front side of fixation screwhole 914. With the drill target 1116 thus positioned, the guide pin 504 is directed by the drill guide 1108 precisely through the center of the fixation screwhole 914.

The rigid drill targeting device 1104 can be rotated front-to-back while maintaining the drill target 1116 aligned in the center of the fixation screwhole 914. The trajectory of the guide pin 504 can thus be varied through a front-to-back arc 924 as depicted at least within FIG. 9E.

As depicted in FIG. 9F the rigid drill targeting device 1104 can also be rotated side-to-side while maintaining the drill target 1116 aligned in the center of the fixation screwhole 914. The trajectory of the guide pin 504 can thus be varied through the side-to-side arc 934.

In either variation of trajectory, the rigid drill targeting device 1104 will maintain the direction of the guide pin 504 precisely through the center of the fixation screwhole 914.

The drill target 1116 can similarly be placed through the utility screwhole 920 in modified fusion cage 1004 (e.g. FIG. 10A) to engage the front side of the central hole 1020 of rotating bearing or snap ring 1018 (e.g. FIG. 10B). The guidance benefits describe for placing a guide pin 504 through the fixation screwhole 914 in modified fusion cage 904 can also be achieved for the fusion cage 1004.

By using the rigid drill targeting device 1104, x-ray guidance is not required and therefore movement of surgeon and assistants away from the operative field is not required. Also, it is not required that the surgeon have extraordinary hand-eye coordination or exceptional skill. Also, operative time for placing the guide pin 504 is reduced. Eliminating the x-ray machine from the operative field and reducing the operative time combine to reduce the likelihood of wound contamination and infection.

The placement of a fixation screw 508 in a minimum diameter fenestration, such as fixation screwhole 914 in modified fusion cage 904 or fixation screwhole 1014 in modified fusion cage 1004, can be accomplished with repeatable speed and precision and with relative ease. The benefits of a tight fit between fixation screw 508 and modified fusion cage 904 or modified fusion cage 1004 can thus be realized.

As depicted in FIG. 11B, movement of the rigid drill targeting device 1104 in the front-to-back direction is limited by the diameter and length of the utility screwhole 920 relative to the diameter of the drill arm 1112. Rotation of the drill targeting device 1104 toward the front of the modified fusion cage 904, when trying to achieve the maximum front trajectory 926 (e.g. FIG. 9E), can be stopped short by the drill arm 1112 contacting the bottom side of the utility screwhole 920. Similarly, a rotation of the rigid drill targeting device 1104 toward the back of the modified fusion cage 904, when trying to achieve the maximum back trajectory 928 (e.g. FIG. 9E), can be stopped short by the drill arm 1112 contacting the top side of the utility screwhole 920. When this happens, the available arc 924 (FIG. 9E) for varying the trajectory of a guide pin 504 in the front-to-back direction is reduced. In turn the ability of the surgeon to pick his desired entry point into a backbone 104 (e.g. FIG. 8), and thus to avoid important adjacent anatomical structures, is reduced.

Additionally, as the drill arm 1112 passing through the utility screwhole 920 is made smaller in diameter, the available arc 924 (e.g. FIG. 9E) is increased. The likelihood, however, of inadvertently bending the drill arm 1112 increases. A bent drill arm 1112 would result in a mis-direction of the guide pin 504.

Further, the drill target 1116 can inadvertently slip off of its engagement on the front side of the fixation screwhole 914 (e.g. FIG. 11B) or on the front side of the central hole 1020 in the rotating bearing or snap ring 1018 (e.g. FIG. 10B). Such a disengagement, if not recognized by the surgeon, could result in a mis-direction of the guide pin 504.

As shown in FIG. 11A, the rigid drill targeting device 1104 has the advantage of simplicity of construction. It also has the advantage of rigidity of its components which best maintains the alignment of the drill guide 1104 with the drill target 1116 following repeated use. However, while much better than no targeting device, the previously described design limitations of the rigid drill targeting device 1104 somewhat reduce its utility. Consequently, an alternative targeting device that overcomes these limitations is desirable.

FIG. 12A shows the left side view of an articulating drill targeting device 1204. At the front is a drill guide 1208 that slides in a guide body 1212 and is secured by a locking lever 1216. The guide body 1212 is linked to an inserter body 1220 at the bottom by two horizontal arms 1224 at the top and by two vertical arms 1228 at the back of the instrument. All arm connections are made with hinge pins 1232.

The articulating drill targeting device 1204 is used in conjunction with a modified fusion cage 904 or a modified fusion cage 1004, an insertion handle 1236, a spacer sleeve 1240, a driver cap 1244, and a guide pin 504.

Figure 12B:
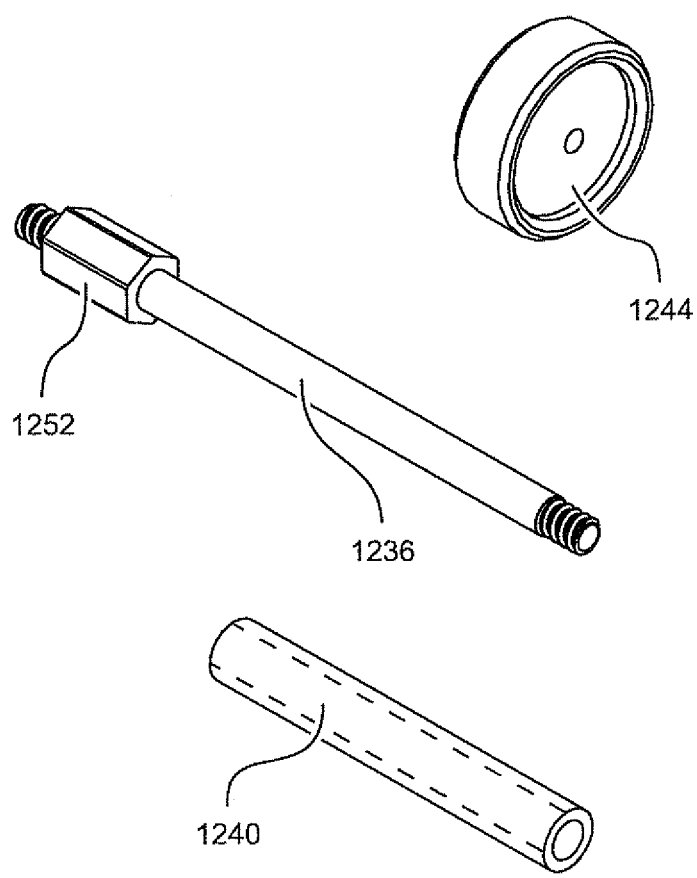
FIG. 12B shows an example of an insertion handle that screws into a modified fusion cage.

As shown in FIGS. 12A and 12B, an insertion handle 1236 is screwed in to a modified fusion cage 904 or into a modified fusion cage 1004 using an open-end wrench applied to the hex section 1252. The articulating drill targeting device 1204 is slid down the insertion handle 1236 by way of a hole 1248 through the inserter body 1220 until it abuts the hex section 1252 of the insertion handle 1236. A spacer sleeve 1240 slides over the insertion handle 1236 and abuts the inserter body 1220. A driver cap 1224 is screwed onto the insertion handle 1236 and abuts the spacer sleeve 1240.

The inserter body 1220 is thus maintained firmly in the desired position relative to the modified fusion cage 904 or modified fusion cage 1004. As FIG. 12A shows, the drill guide 1208 directs a guide pin 504 precisely along the trajectory 1256 through the center of the fixation screwhole 914 in modified fusion cage 904 or the fixation screwhole 1014 in modified fusion cage 1004.

The articulating drill targeting device 1204 is in the geometric configuration of two interconnected parallelograms as defined by the horizontal arms 1224 and guide body 1212 interconnected by hinge pins 1232 to the vertical arms 1228 and the inserter body 1220. Utilizing this parallelogram principal, the articulating drill targeting device 1204 can be rotated front-to-back while maintaining the guide pin 504 in precise alignment with the center of the fixation screwhole 914.

The further described embodiments of the articulating drill targeting device 1204 when used with modified fusion cage 904 are identical when used with fusion cage 1004.

As shown in FIG. 12A, when rotated toward the front of modified fusion cage 904, the articulating drill targeting device 1204 can easily achieve the alignment of the guide pin 504 along the maximum front trajectory 926 without impediment. Similarly, rotation of the articulating drill targeting device 1204 toward the back of the modified fusion cage 904 achieves alignment of guide pin 504 with the maximum back trajectory 928 without impediment.

As FIG. 12A illustrates, the articulating drill targeting device 1204 is connected to the modified fusion cage 904 by the robust insertion handle 1236. There is no small diameter drill arm 1112 (e.g. FIG. 11B) as used in the rigid drill targeting device 1104 that is at risk of becoming bent and misguiding a guide pin 504.

As shown in FIGS. 12A and 12B, the screw connection of insertion handle 1236 to the fusion cage 904 maintains the articulating drill targeting device 1220 to be securely attached to modified fusion cage 904. An inadvertent disengagement between the targeting device and cage, as can occur with the rigid drill targeting device 1104, is thus avoided.

Figure 12C:
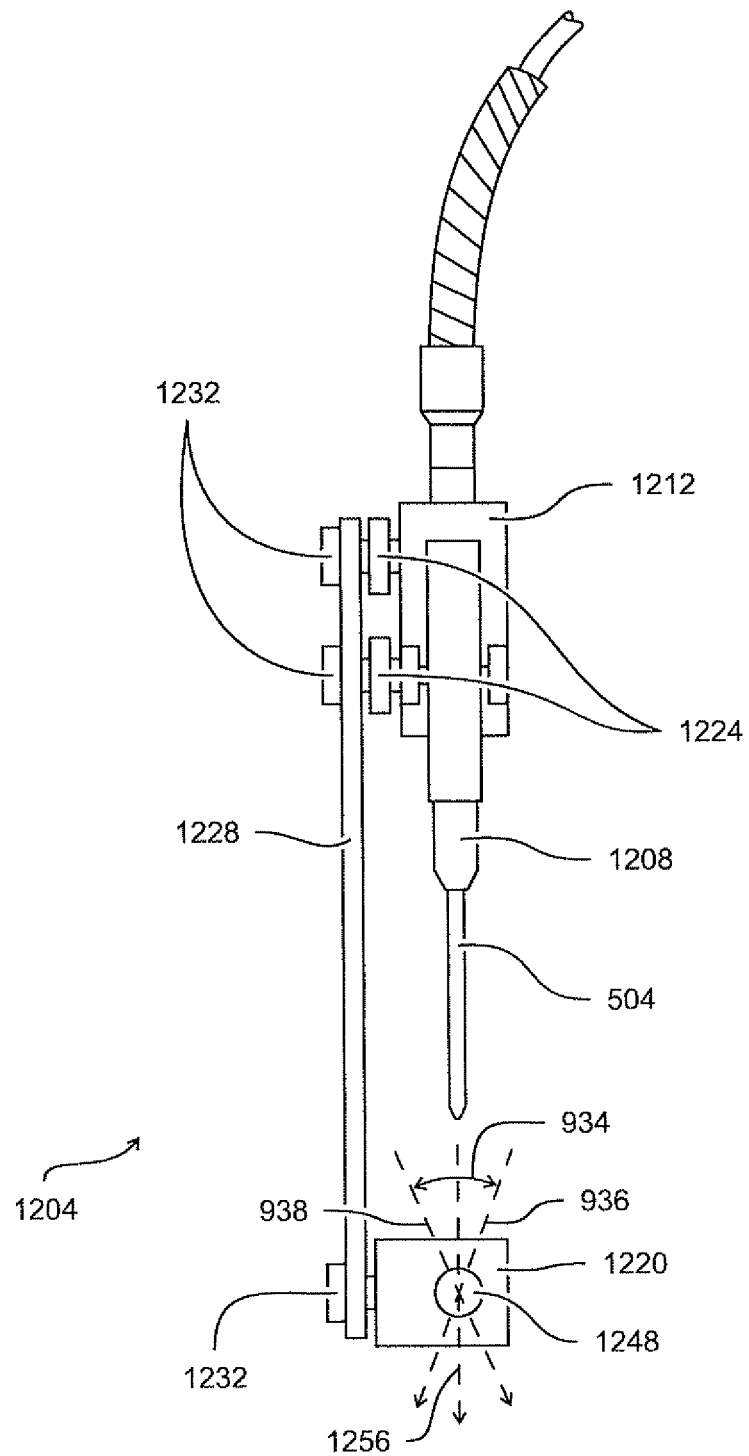
FIG. 12C shows a back view of the articulating drill targeting device of FIG. 12A.

FIG. 12C shows the back view of the articulating drill targeting device 1204 with the horizontal arm 1224 and the vertical arms 1228 connected with the hinge pins 1232 to the guide body 1212 and the inserter body 1220. The articulating drill targeting device 1204 slides onto the insertion handle 1236 using hole 1248 in the inserter body 1220. Drill guide 1208, and therefore guide pin 504, are aligned with hole 1248 as depicted by guide pin trajectory 1256 (also shown at least within FIG. 12A).

As shown in FIGS. 9B and 10A, when insertion handle 1236 is screwed into utility screwhole 920 in modified fusion cage 904, insertion handle 1236 becomes aligned with the center of fixation screwhole 914. With the drill guide 1208 being in alignment with hole 1220 as shown in FIG. 12C, drill guide 1208 is thus also in alignment with insertion handle 1236 and, therefore, also in alignment with the center of fixation screwhole 914 in modified fusion cage 904.

As shown in FIG. 12C, since the articulating drill targeting device 1204 rotates side-to-side around the center of insertion handle 1236 which is aligned with the center of fixation screwhole 914, then the articulating drill targeting device 1204 also rotates about the center of fixation screwhole 914.

The articulating drill targeting device 1204 is thus unimpeded in rotating side-to-side while maintaining alignment of drill guide 1208 with fixation screwhole 914. Articulating drill targeting device 1204 easily maintains this alignment while rotating from the maximum left guide pin trajectory 936, through arc 934, to the maximum right guide pin trajectory 938.

Figure 6:
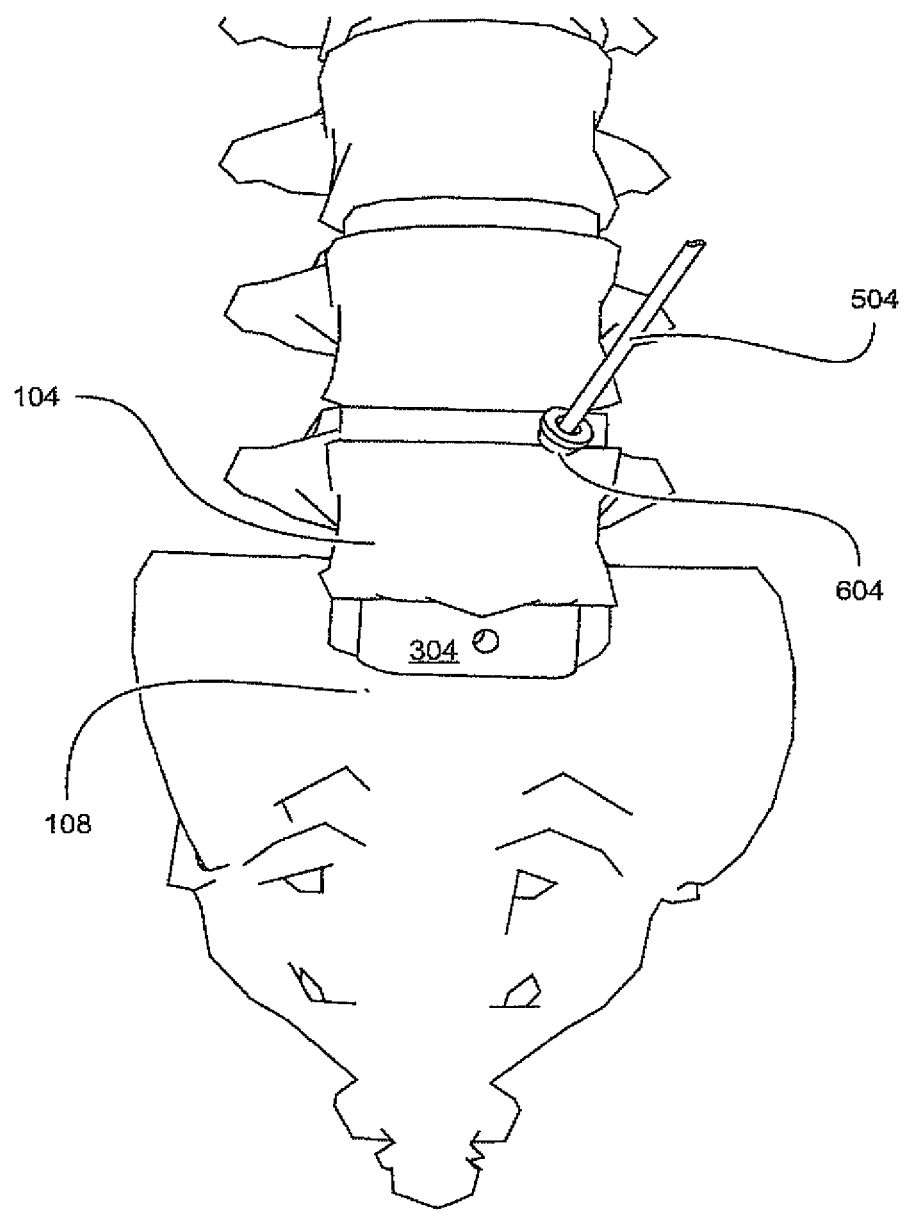
FIG. 6 shows a view of a spine with a fusion cage inserted therein.
Figure 12D:
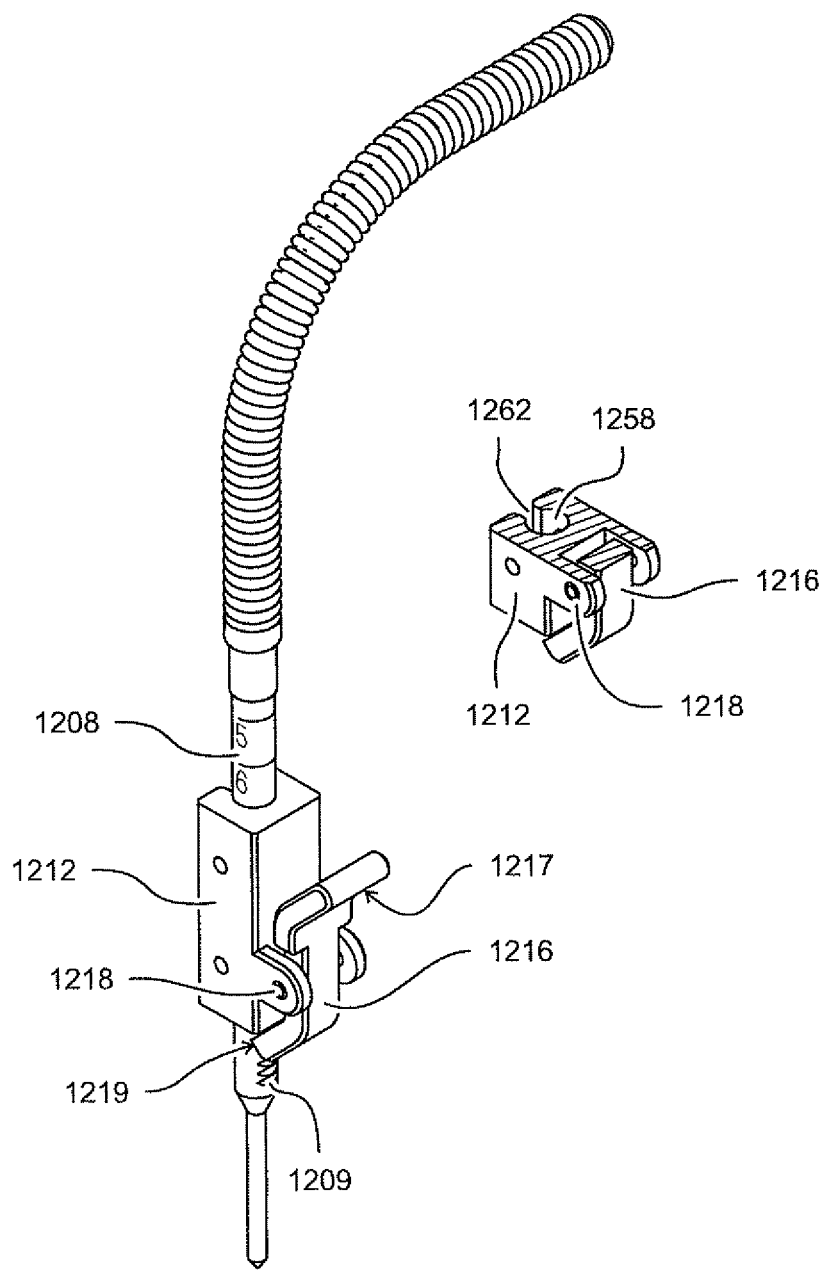
FIG. 12D shows a left side view and a cross-sectional view of a guide body.
Figure 12E:
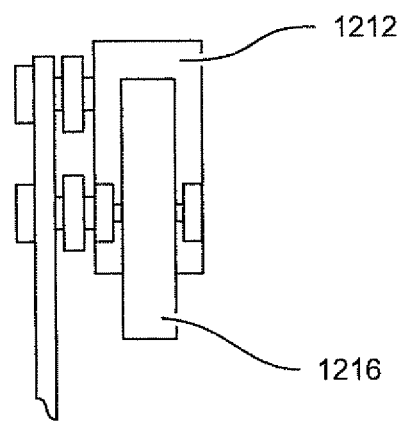
FIGS. 12E-12F show back and front views, respectively, of the guide body of FIG. 12D.
Figure 12F:
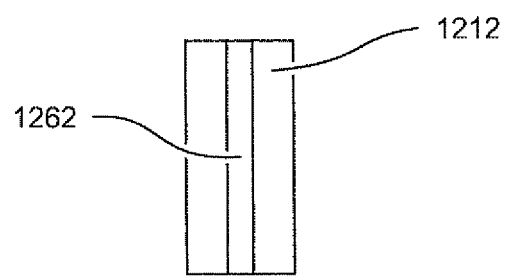

FIG. 12D shows a left side view and a cross-sectional view of the guide body 1212. FIG. 12E shows the back view and FIG. 12F show the front view of guide body 1212. The drill guide 1208 is able to slide up and down in hole 1258. A spring-loaded locking lever 1216 engages serrations 1209 in the side of drill guide 1208. The geometry of this engagement is such that the drill guide 1208 can be pushed down, without impediment, firmly into position against the backbone 104 at the desired guide pin entry point 604 (e.g. FIG. 6).

The locking lever 1216 prevents the drill guide 1208 from backing up. The articulated drill targeting device 1204, therefore, remains firmly in position by acting as a C-clamp in squeezing the L5 backbone 104 between the modified fusion cage 904 and the drill guide 1208.

Figure 12G:
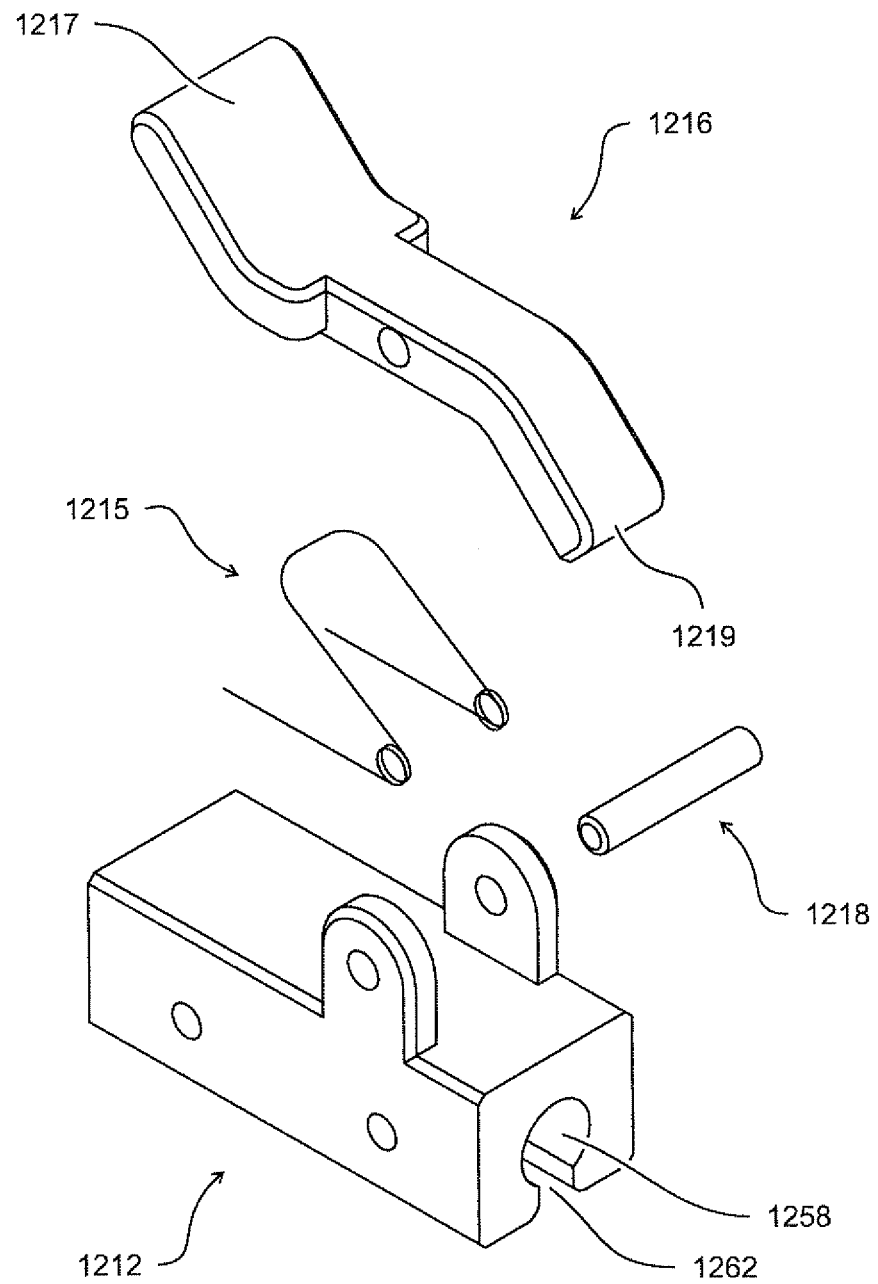
FIG. 12G shows an exploded perspective view of the guide body of FIGS. 12D-12F.

FIG. 12G shows an exploded perspective view of guide body 1212. A spring 1215 fixed by pin 1218 maintains the top end 1217 of locking lever 1216 to default to a raised position. The bottom end 1219 of locking lever 1216 is thereby maintained depressed against the serrations 1209 on the drill guide 1208 (e.g. FIG. 12D) until such time as the surgeon depresses the top end 1217 of the locking lever 1216.

Following insertion of the guide pin 504, the clamping action of the articulated drill targeting device 1204 is released by the surgeon depressing the top end 1217 of the locking lever 1216 which rotates on pin 1218 to raise the bottom end 1219 away from the serrations 1209 on drill guide 1208. The drill guide 1208 can now be pulled up out of the drill body 1212 and off of the guide pin 504.

FIGS. 12D, 12F, and 12G show a guide pin exit slot 1262 connecting the front side of the guide body 1212 with the drill guide hole 1258. Following removal of the drill guide 1208, the articulating drill targeting device 1204 is rotated to the back allowing the guide pin 504 to exit the drill guide hole 1258 by way of this guide pin exit slot 1262. The articulating drill targeting device 1204 can now be removed along with the inserter handle 1236 in the reverse order of their attachment to modified fusion cage 904.

Figure 12H:
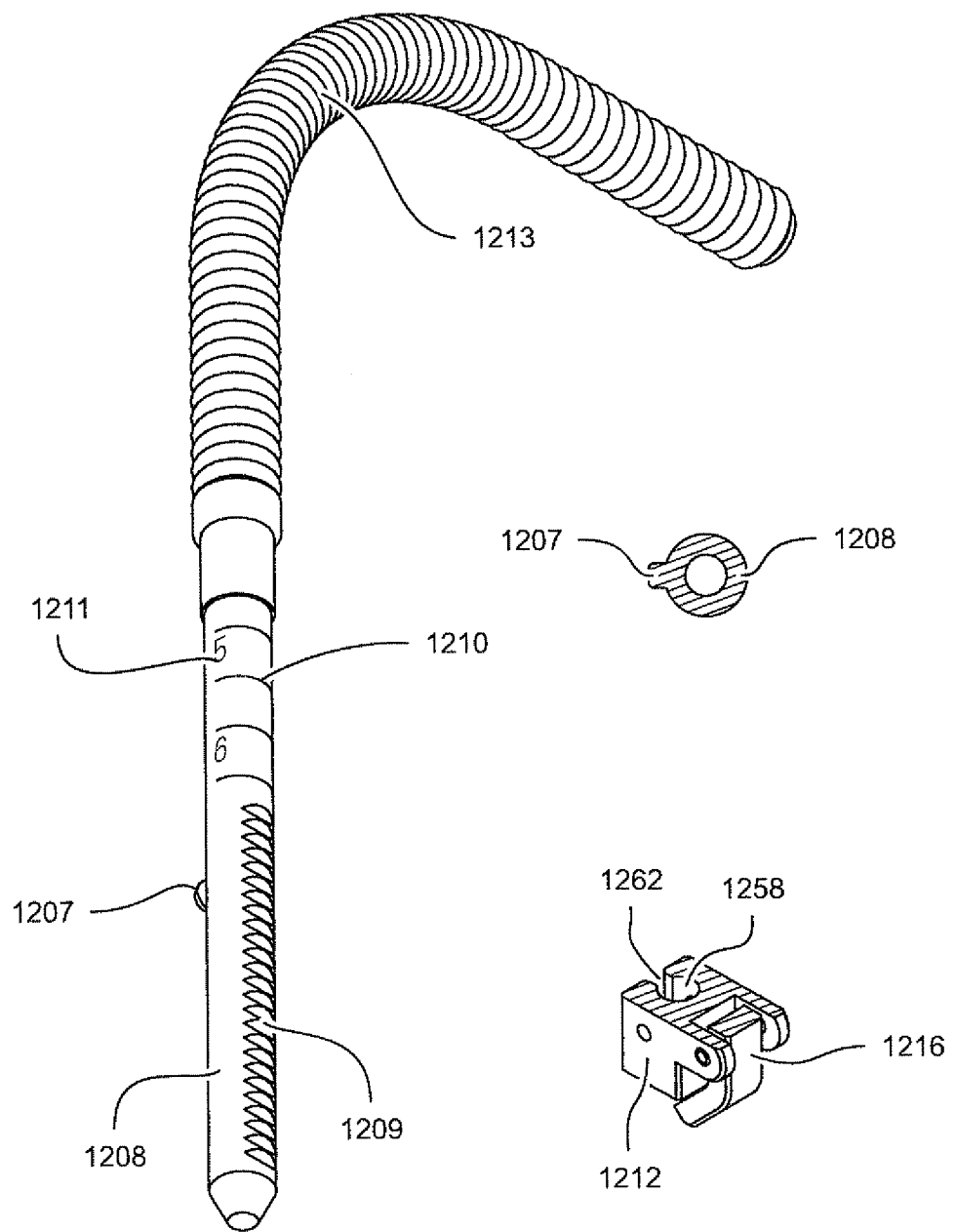
FIG. 12H shows a drill guide having depth gauge markings and numbers, and a flexible guide pin tissue protector that can be screwed onto or otherwise attached to the drill guide.

FIG. 12H shows the drill guide 1208 with an alignment fin or pin 1207 that engages guide pin exit slot 1262 as drill guide 1208 slides up and down through the hole 1258 in guide body 1212. Drill guide 1208 is thereby prevented from rotating in the hole 1258. The serrations 1209 on the side of drill guide 1208 are thereby maintained facing and engaging locking lever 1216.

FIG. 12H shows depth gauge markings 1210 and numbers 1211 on drill guide 1208. When the drill guide 1208 is clamped into position against the backbone 104 at the desired guide pin entry point 604 (e.g. FIG. 6), the distance from the guide pin entry point 604 to the center of fixation screwhole 914 in modified fusion cage 904 can be read off the drill guide 1208 where the depth gage markings 1210 align with the top of guide body 1212.

Knowing the height of the selected modified fusion cage 904 and knowing the desired distance that fixation screw 508 needs to extend past this cage, the surgeon can easily calculate the required length of fixation screw 508.

By knowing the required length of the fixation screw 508, the surgeon knows to what depth guide pin 504 must be drilled. Repeated use of x-rays to follow the advance of guide pin 504 to the desired depth is not required. Measuring the length of guide pin 504 thus inserted, in order to determine the required length of fixation screw 508, is not necessary. Thus, the previously described negative factors associated with the use of x-ray guidance are further avoided.

FIG. 12H shows a flexible guide pin tissue protector 1213 that can be screwed onto or otherwise attached to drill guide 1208. This guide pin tissue protector 1213 prevents important adjacent tissues from being damaged by winding around the spinning guide pin 504 as it is being drilled into the bone.

Figure 12I:
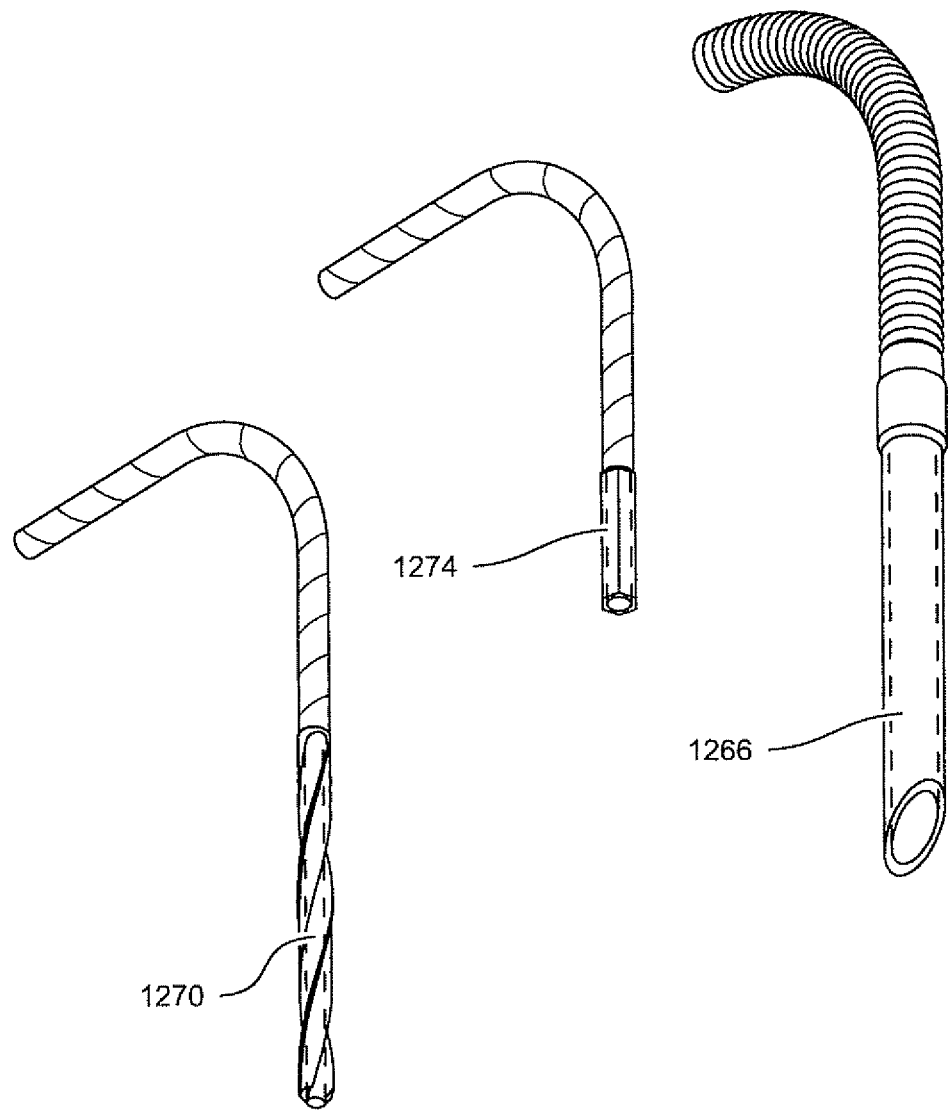
FIG. 12I shows a flexible screw insertion tissue protector that can be slid over a guide pin.

FIG. 12I shows a flexible screw insertion tissue protector 1266 that can be slid over guide pin 504 following insertion of guide pin 504, removal of drill guide 1208, and removal of articulating drill targeting device 1204. This flexible screw insertion tissue protector 1266 accommodates the passage of a flexible drill bit 1270. It also accommodates the passage of fixation screw 508 and attached flexible screwdriver 1274 down over guide pin 504. Adjacent soft tissues are thus protected from damage by the spinning drill bit 1270. Adjacent soft tissues are also protected by the spinning fixation screw 508 and screwdriver 1274 during screw insertion.

A Potential Method for Implementing Various of the Preferred Embodiments

Figure 13:
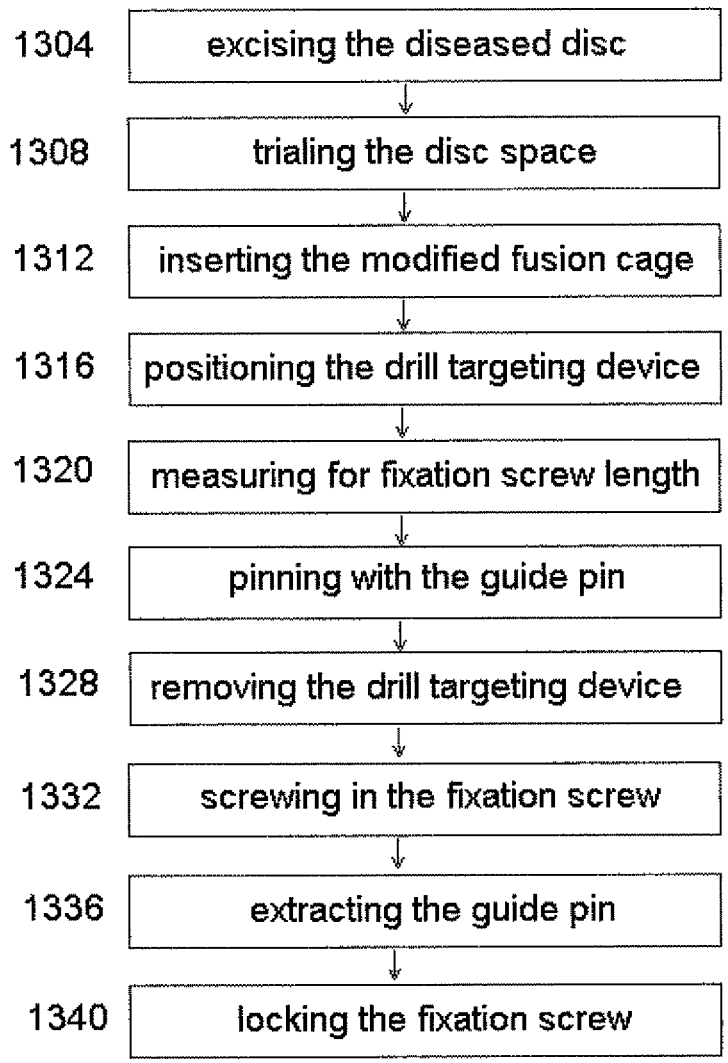
FIG. 13 depicts a potential method for implementing the preferred embodiments.

FIG. 13 depicts an example method 1300 for implementing various of the embodiments disclosed herein. This example method is applicable to both modified fusion cages 904 and 1004, and can be briefly summarized as follows. Step 1304 comprises excising the diseased disc. Step 1308 comprises trialing the disc space. Step 1312 comprises inserting the modified fusion cage. Step 1316 comprises positioning the drill targeting device. Step 1320 comprises measuring for fixation screw length. Step 1324 comprises pinning with the guide pin. Step 1328 comprises removing the drill targeting device. Step 1332 comprises screwing in the fixation screw. Step 1336 comprises extracting the guide pin. Step 1340 comprises locking the fixation screw.

Figure 14:
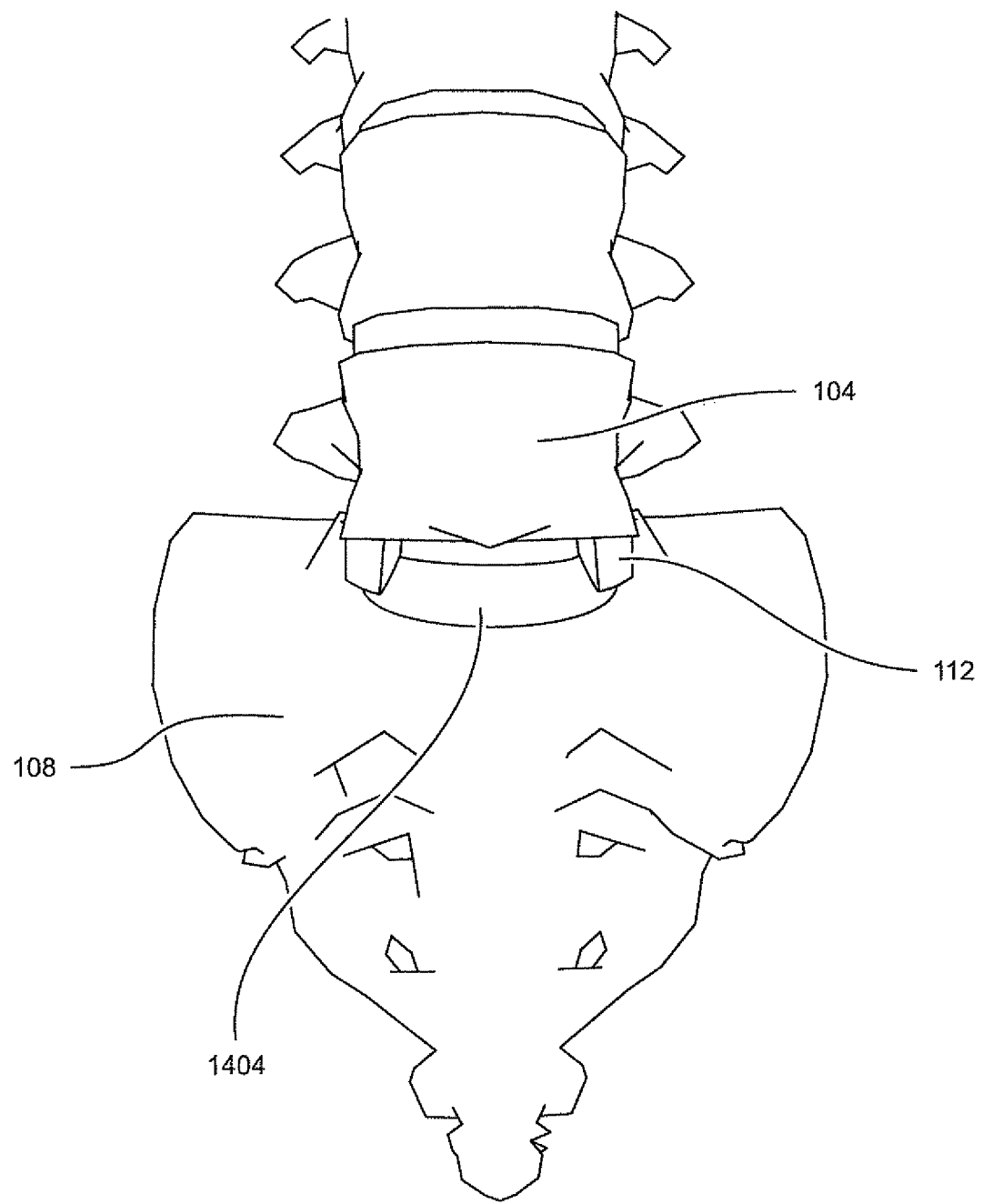
FIG. 14 shows excising a diseased disc, thus creating a space for a cage.

The method 1300 will now be described in more detail. FIG. 14 shows excising the diseased disc 112 from between the backbones 104 and 108 to be fused, thus creating a space 1404 for the cage.

Figure 15:
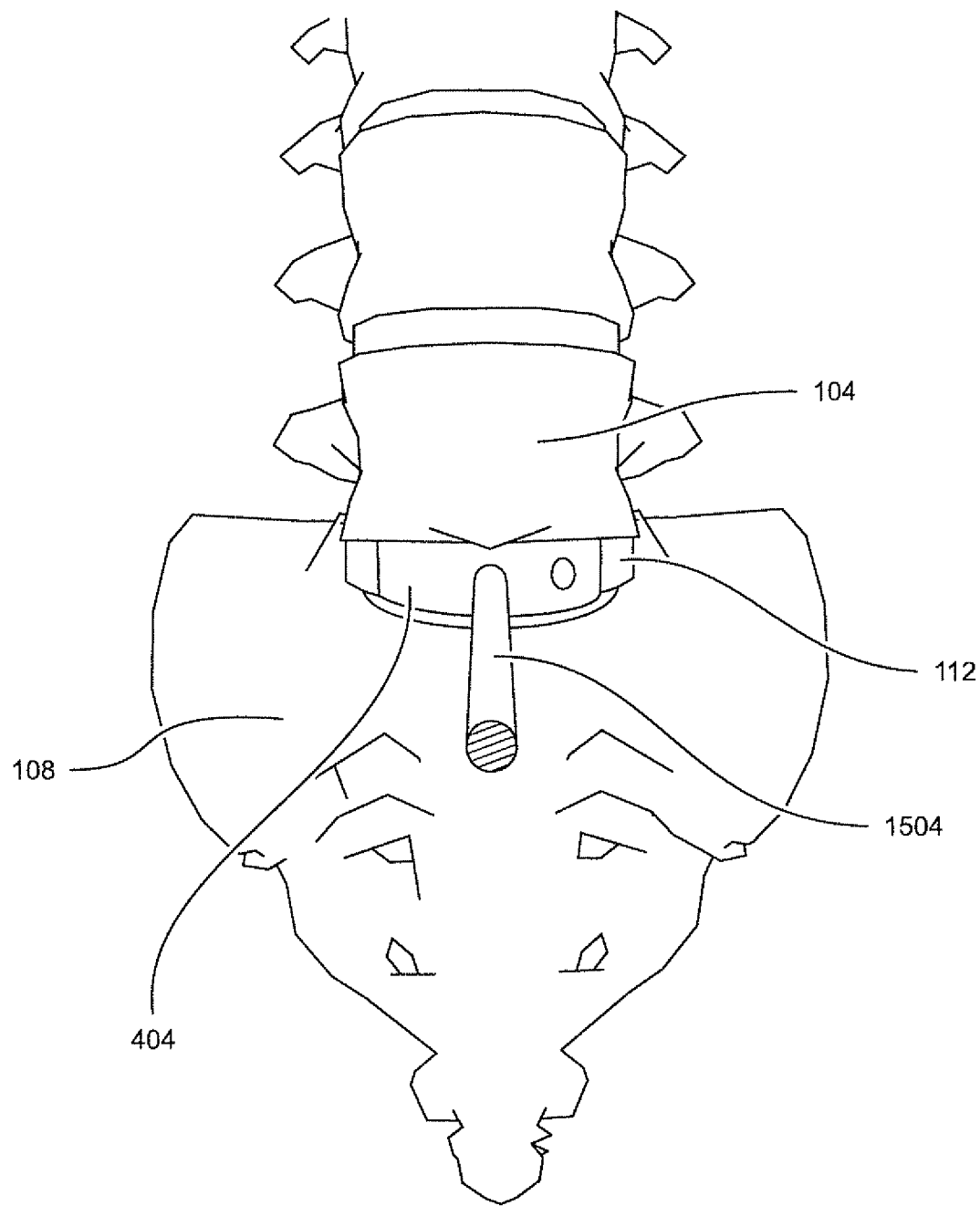
FIG. 15 shows trialing the disc space of FIG. 14 by attaching the trial cage to an insertion handle.

FIG. 15 shows trialing the disc space by attaching the trial cage 404 to an insertion handle 1504. The varying sizes of modified trial cages are repeatedly inserted into the disc space until a proper fit is obtained.

Figure 16:
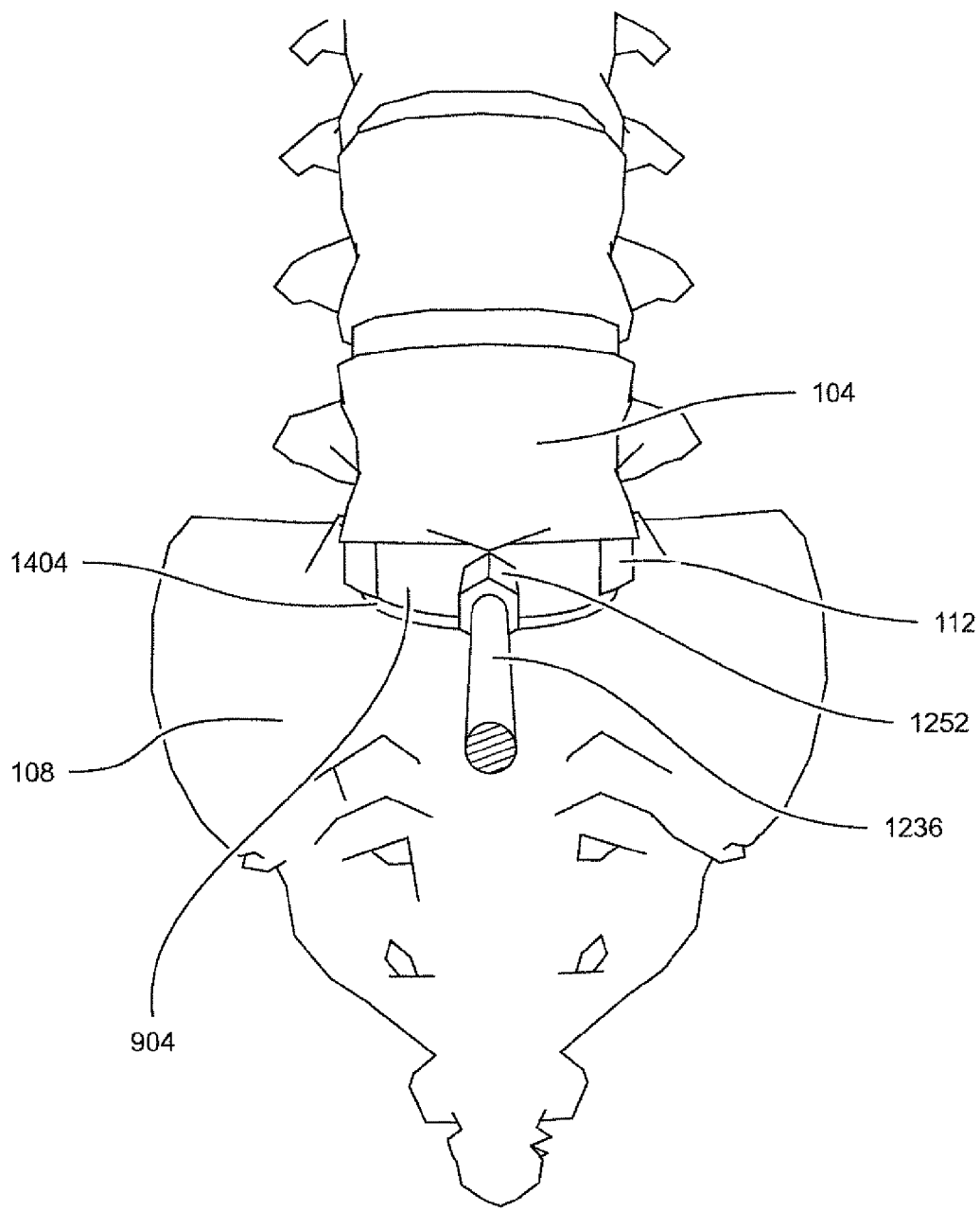
FIG. 16 shows inserting a modified fusion cage into a space using an insertion handle.

FIG. 16 shows inserting the modified fusion cage 904 into space 1404 using an insertion handle 1236.

Figure 17A:
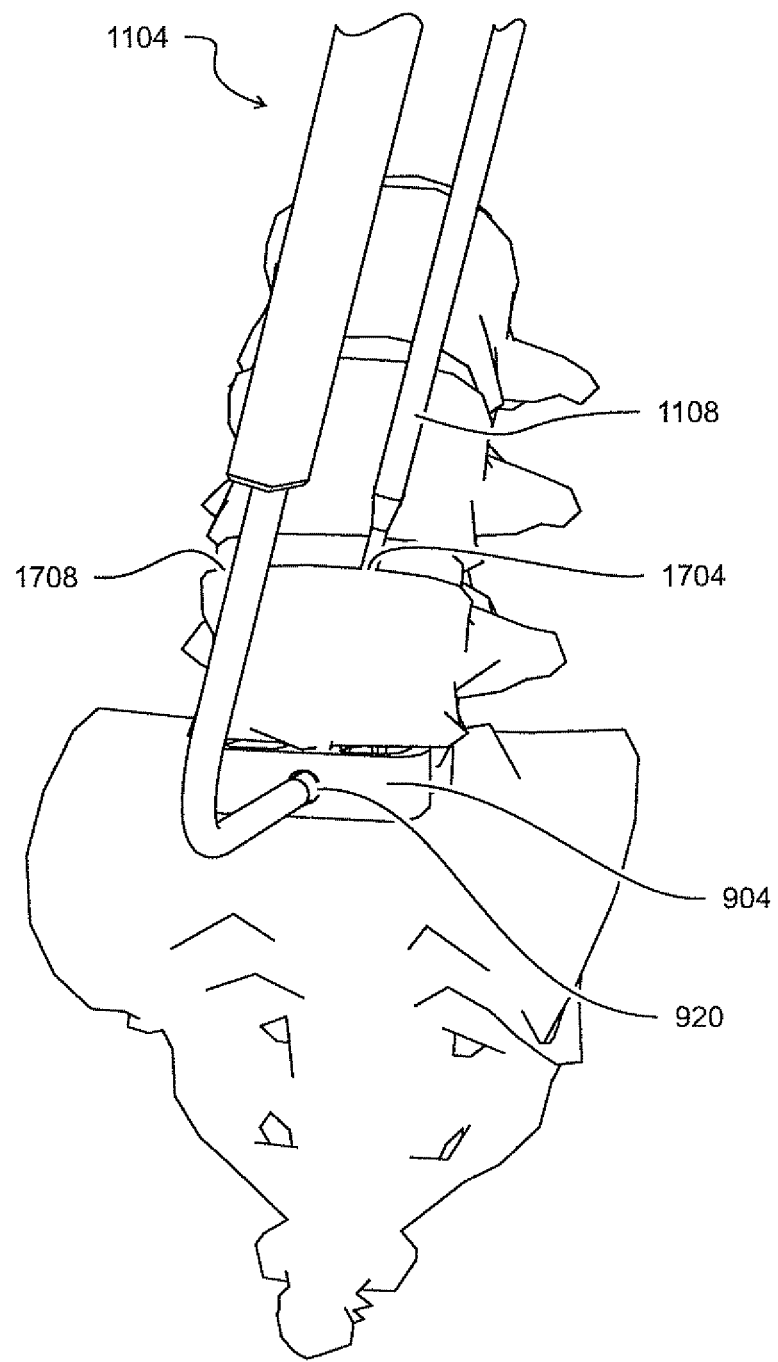
FIG. 17A shows an example position of a rigid drill targeting device rotated to the left side.

FIG. 17A shows positioning the rigid drill targeting device 1104 by inserting the drill target 1116 through the utility screwhole 920 to engage the front side of fixation screwhole 914. In such an environment, the rigid drill targeting device 1104 can now be rotated in the side-to-side direction and front-to-back direction to place the entry point for the guide pin 504 insertion at a position of the surgeon's choosing, while maintaining the alignment of the drill guide 1108 with the fixation screwhole 914 in the modified fusion cage 904.

Figure 17B:
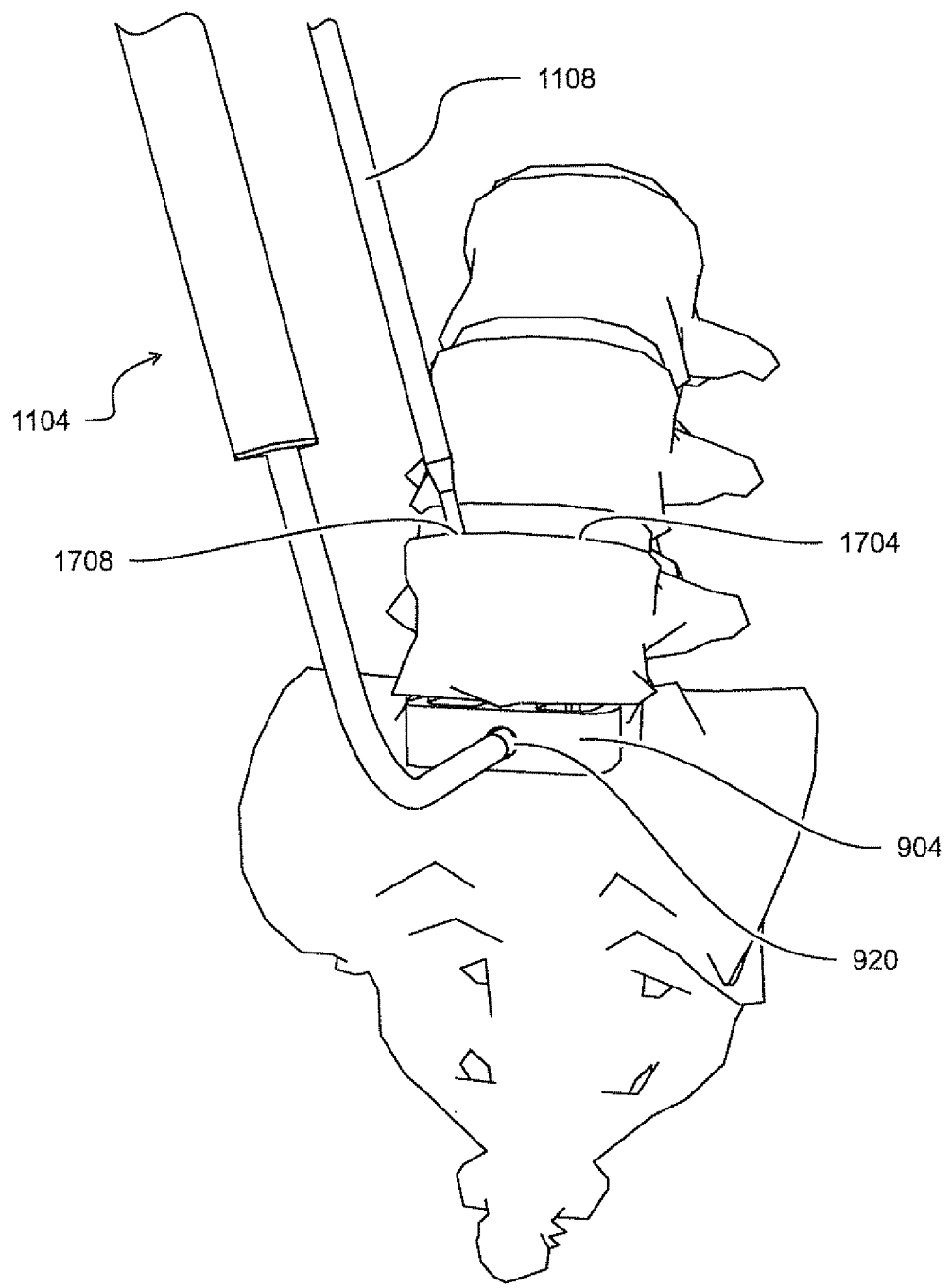
FIG. 17B shows the rigid drill targeting device of FIG. 17A rotated to the right side.

FIGS. 17A and 17B show movement in the side-to-side direction. In FIG. 17A the rigid drill targeting device 1104 has been rotated to the left side to select an entry point 1704. In FIG. 17B the rigid drill targeting device 1104 has been rotated to the right side to select a different entry point 1708. At either entry point, the drill guide 1108 remains precisely aligned with the drill target 1116 and fixation screwhole 914.

Figure 17C:
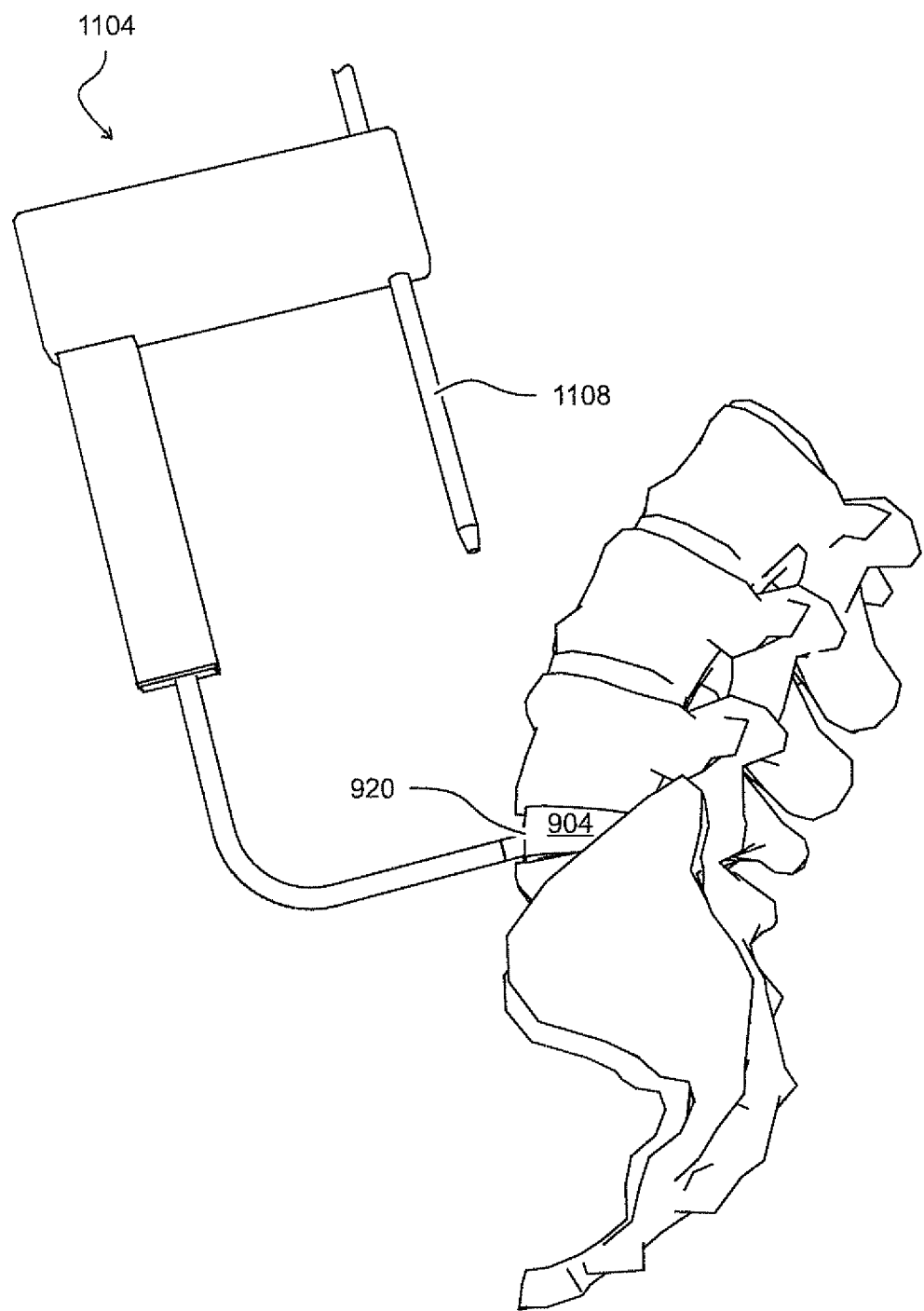
FIGS. 17C and 17D shows the rigid drill targeting device rotated toward the front and back directions, respectively.
Figure 17D:
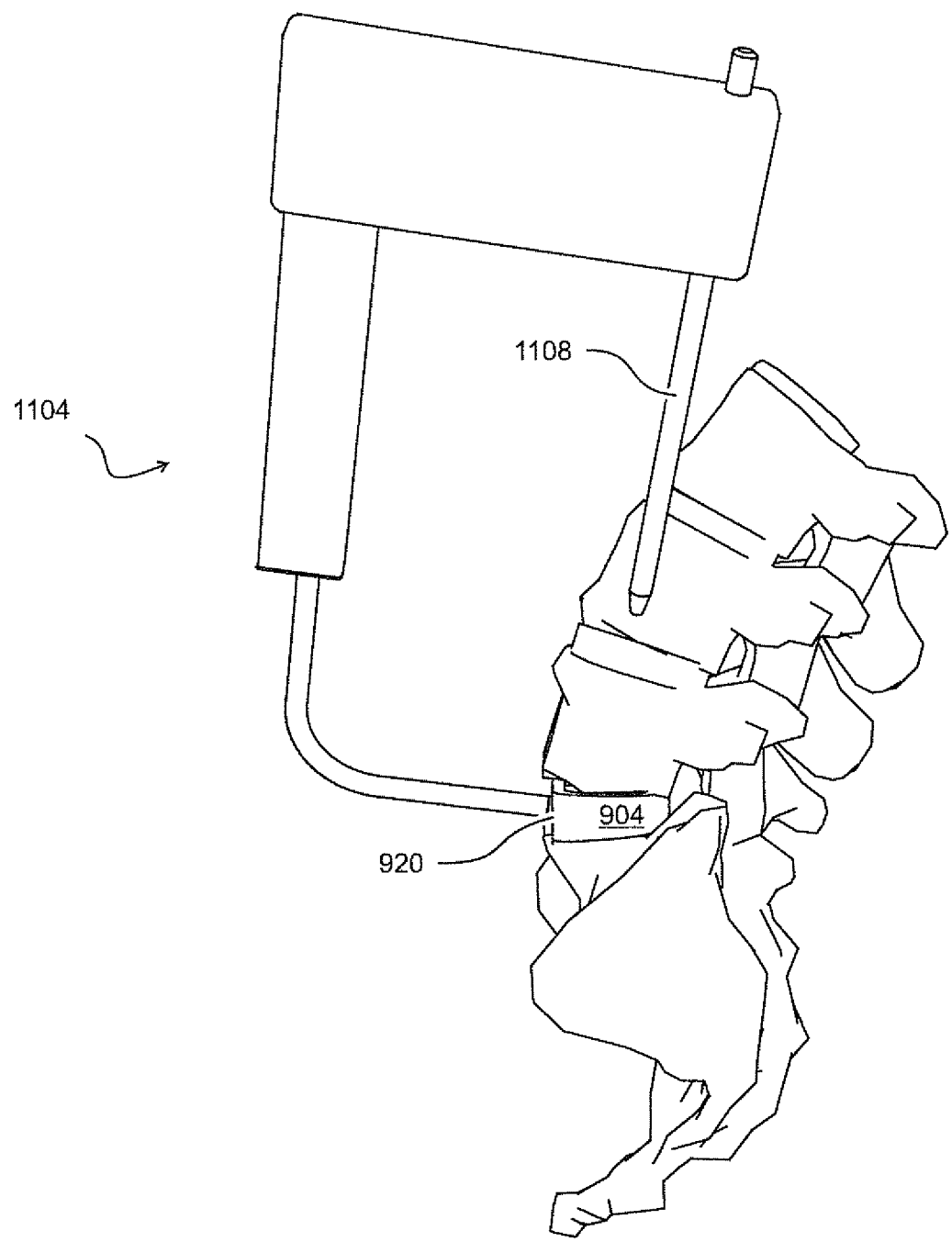

FIGS. 17C and 17D show movement in the front-to-back direction. In FIG. 17C the rigid drill targeting device 1104 has been rotated toward the front. In FIG. 17D the rigid drill targeting device 1104 has been rotated toward the back. Rotation in this front-to-back direction is carried out simultaneously with rotation in the side-to-side direction in order to place the drill guide 1108 at the entry point of the surgeon's choosing.

In FIG. 17A the drill guide 1108 has been slid down against the bone at the chosen entry point 1704 and locked in position with the thumbscrew 1118 (e.g. FIG. 11A). The position of the drill targeting device is stabilized by the clamping of the backbone 104 between the drill guide 1108 and drill target 1116.

Figure 17E:
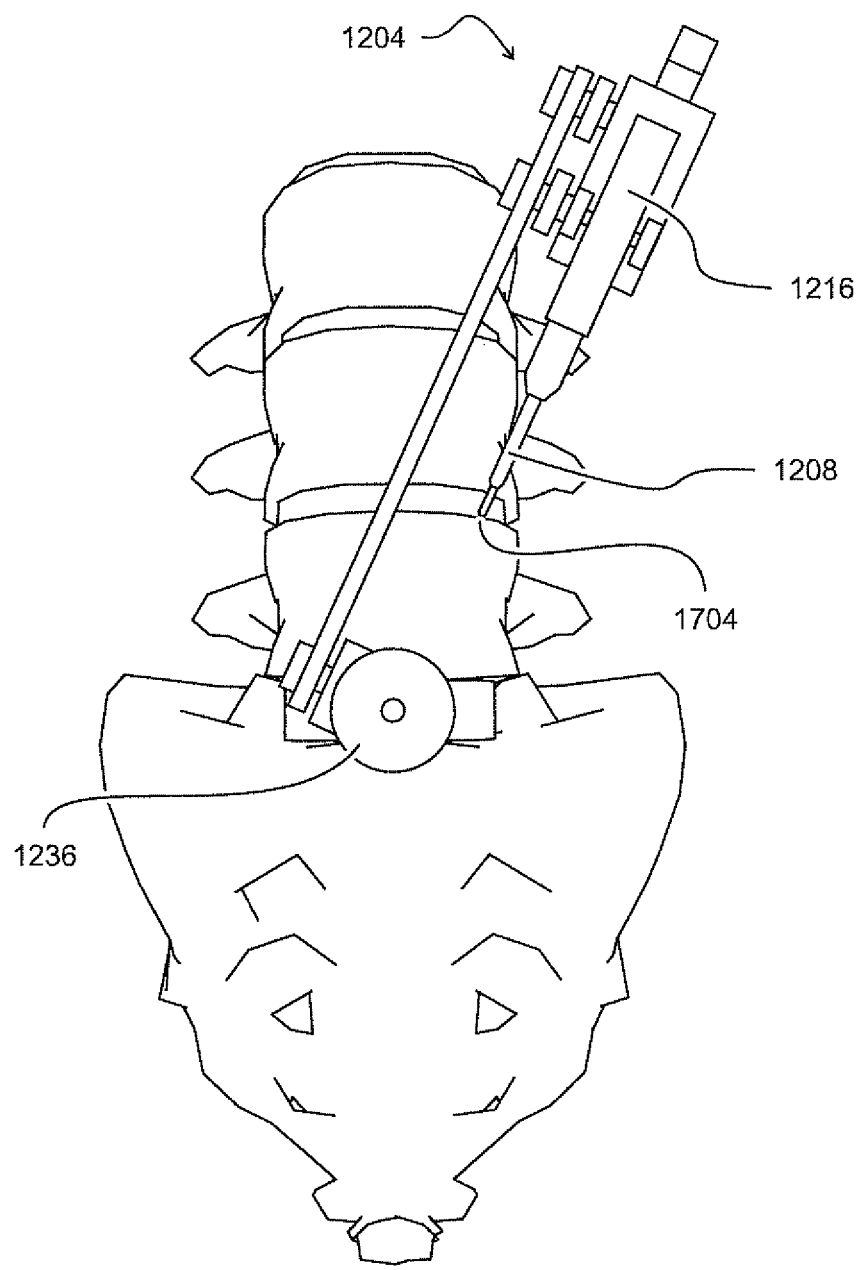
FIG. 17E-17H show example positions of an articulating drill targeting device.

FIG. 17E shows positioning the articulating drill targeting device 1204. The inserter handle 1236 is already in position having been used in step 1312 inserting the modified fusion cage 904. The articulating drill targeting device 1204 is now assembled onto insertion handle 1236 as described in connection at least with FIGS. 12A and 12B.

As with the rigid drill targeting device 1104, the articulating drill targeting device 1204 can now be rotated in the side-to-side direction and in the front-to-back direction to place the entry point for guide pin 504 insertion at a location of the surgeon's choosing, while maintaining the alignment of the drill guide 1208 with the fixation screwhole 914 in the modified fusion cage 904.

Figure 17F:
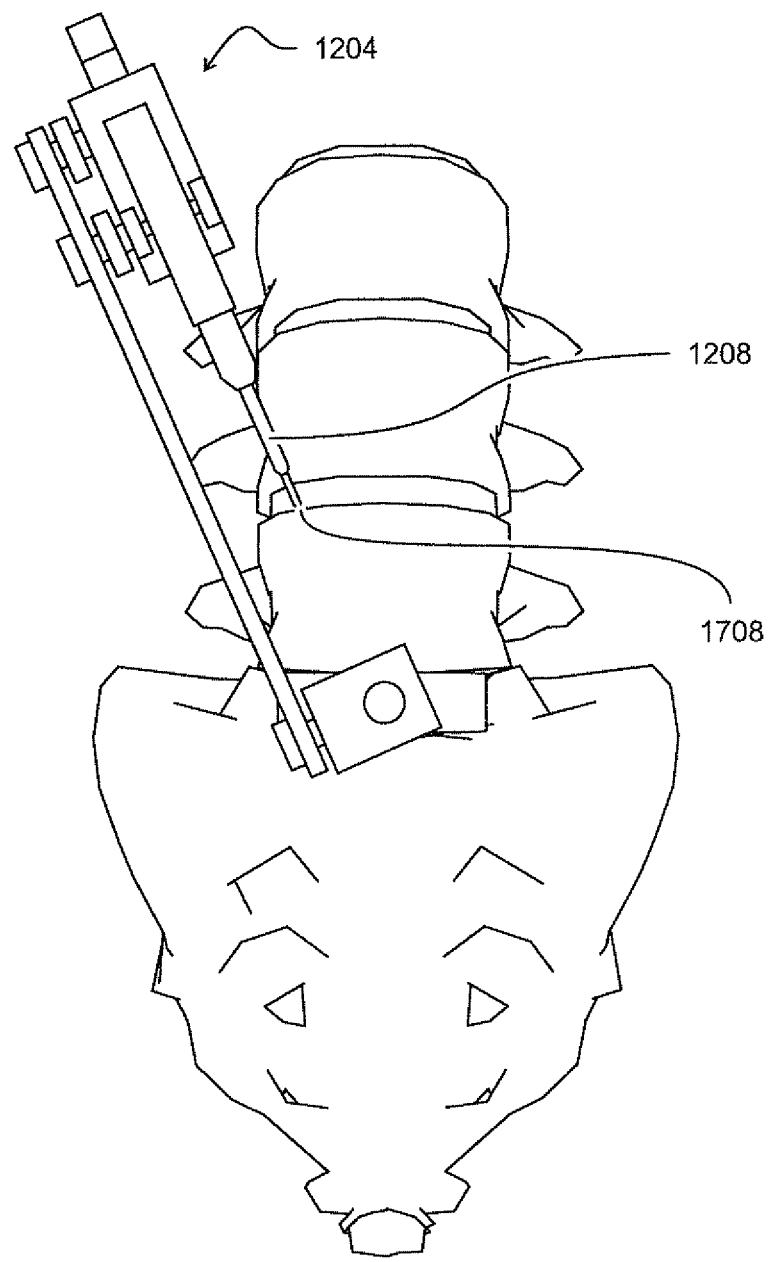

FIGS. 17E and 17F show this movement in the side-to-side direction. In FIG. 17E the articulating drill targeting device 1204 is rotated to the left side to select an entry point 1704. In FIG. 17F the articulating drill targeting device 1204 is rotated to the right side to select a different entry point 1708. At either entry point the drill guide 1208 remains precisely aligned with the fixation screwhole 914.

Figure 17G:
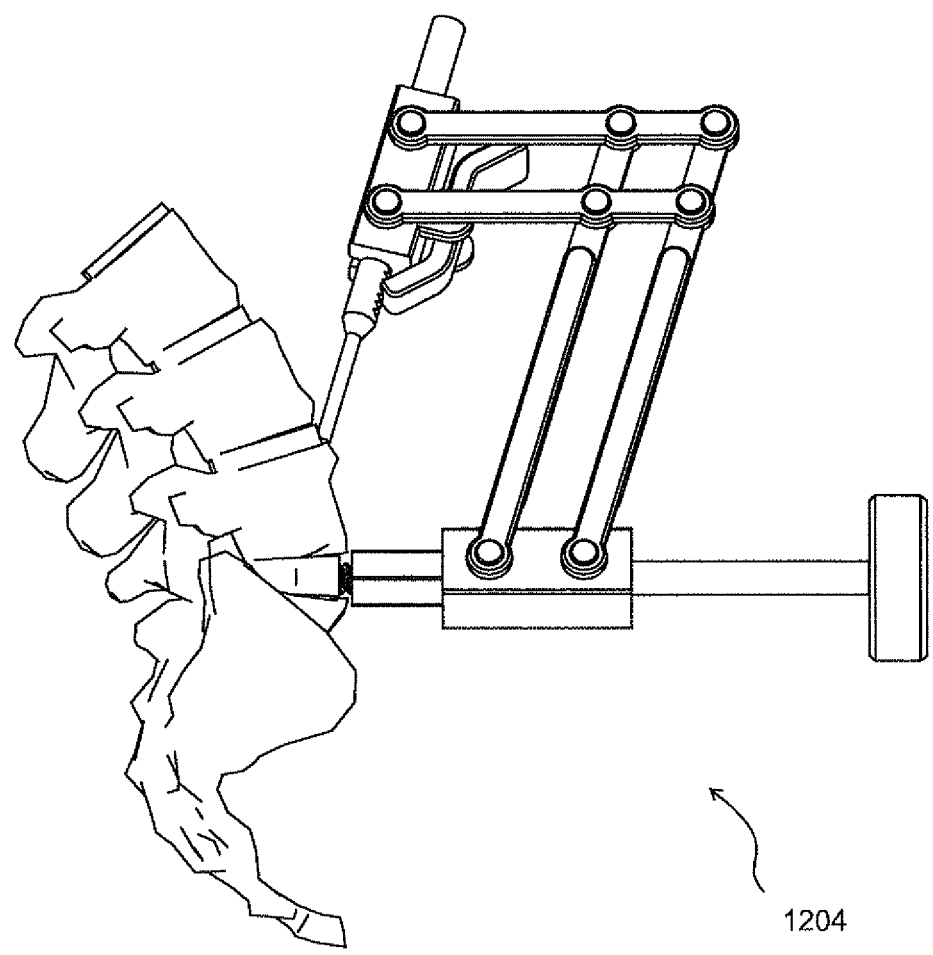
Figure 17H:
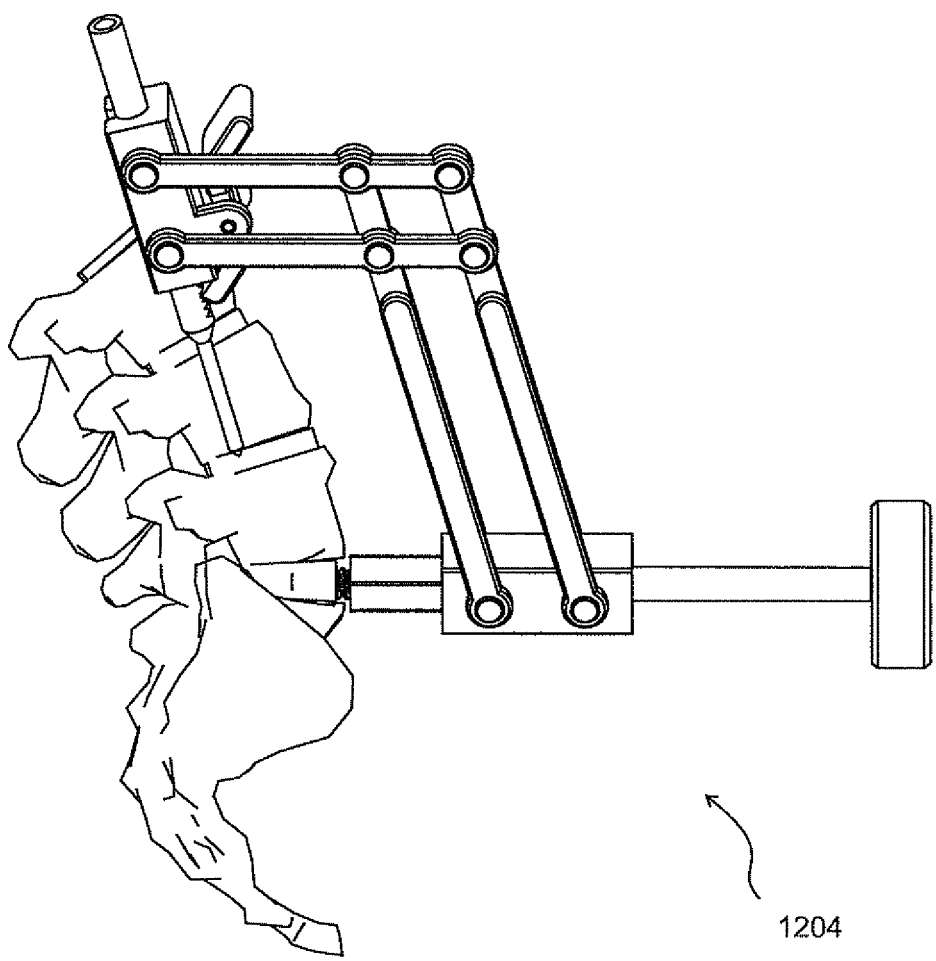

FIGS. 17G and 17H show movement in the front-to-back direction. In FIG. 17E the articulating drill targeting device 1204 has been rotated to the front. In FIG. 17H the articulating drill targeting device 1204 has been rotated to the back. Rotation in this front-to-back direction is carried out simultaneously with rotation in the side-to-side direction in order to place the drill guide 1208 at the entry point of the surgeon's choosing.

In FIG. 17E the drill guide 1208 has been slid down against the bone at the chosen entry point 1704 and is held locked in position by the locking lever 1216, as described at least in connection with FIGS. 12D, 12E, and 12F.

Figure 18:
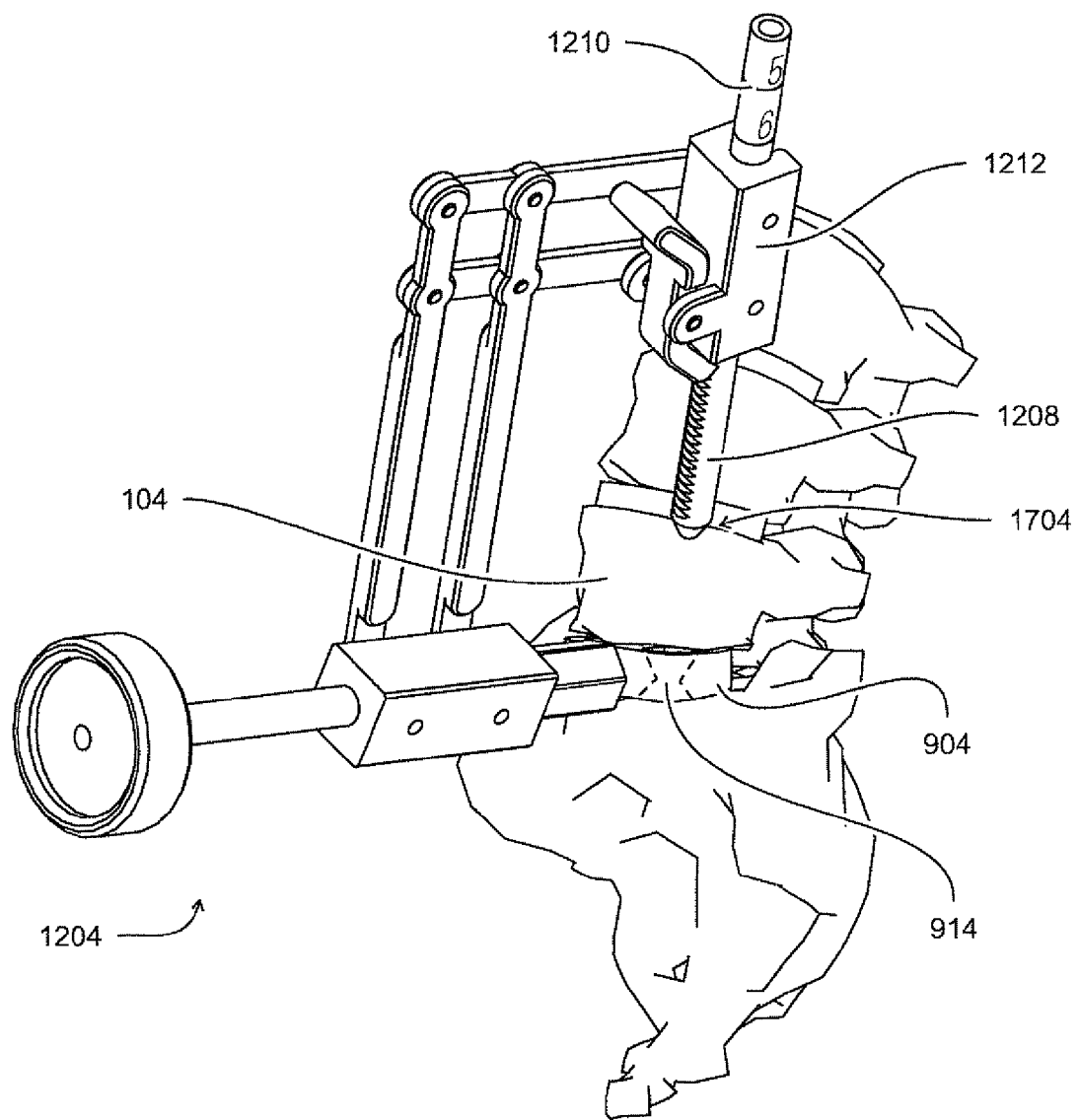
FIG. 18 illustrates obtaining an example measurement for a fixation screw length.

FIG. 18 shows measuring for fixation screw length by reading the value of the depth gauge marking 1210 on drill guide 1208 that is aligned with the top of guide body 1212 as described in connection at least with FIG. 12H. The required depth of insertion of guide pin 504 is next calculated as described in connection at least with FIG. 5 and determining the required length of the fixation screw 508. The same procedure is used with the rigid drill targeting device 1104.

Figure 19:
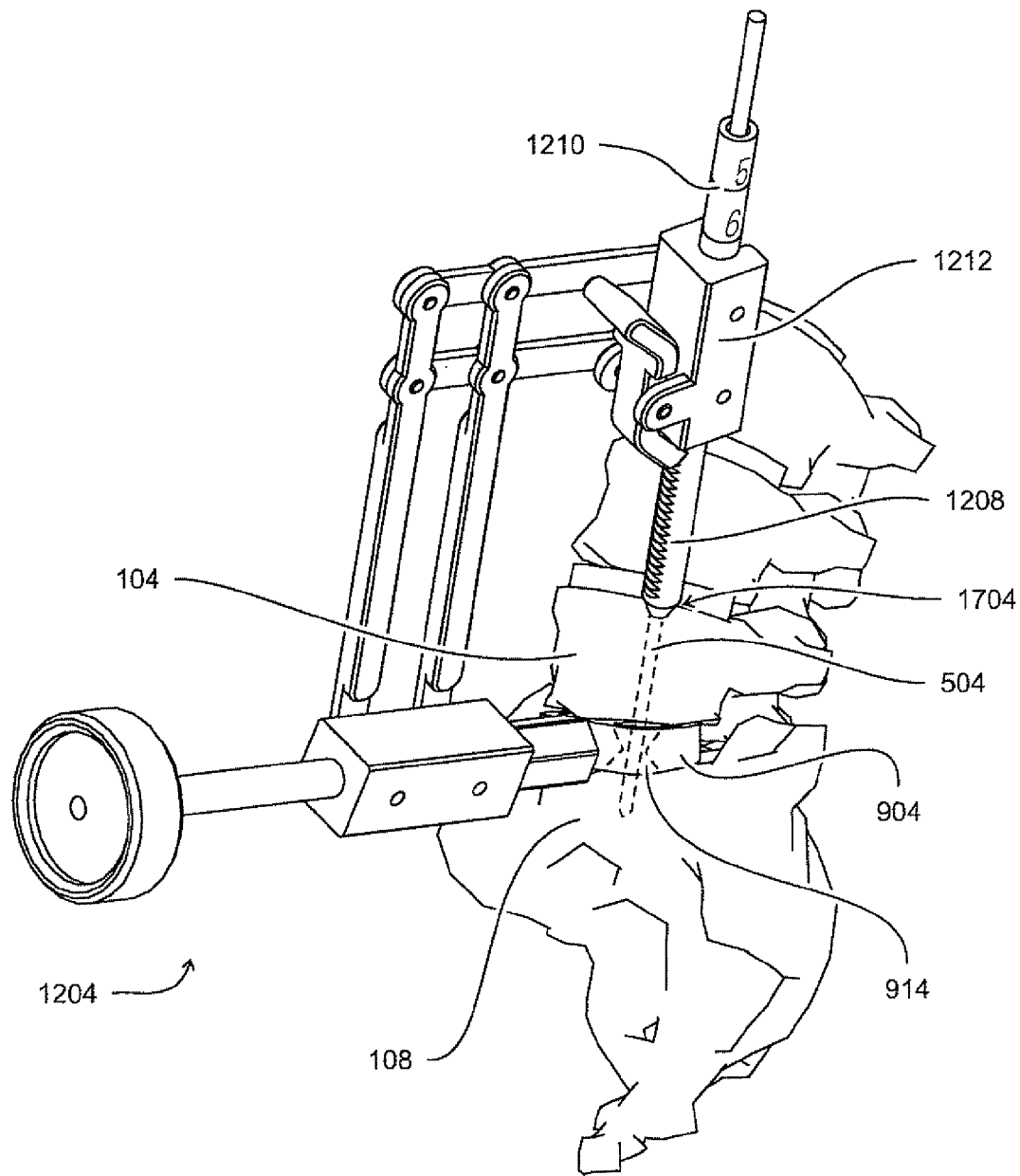
FIG. 19 shows an example use of a guide pin operated in conjunction with the articulating drill targeting device of FIGS. 17E-17H.

FIG. 19 shows pinning the modified fusion cage 904 with a guide pin 504 using the articulating drill targeting device 1204. The guide pin 504 is inserted into the drill guide 1208 and drilled through the backbone 104 on the near side of the modified fusion cage 904, through the fixation screwhole 914 in the modified fusion cage 904, and then into the backbone 108 on the far side of the modified fusion cage 904. The guide pin 504 is inserted to the predetermined depth calculated in step 1320. The same procedure is used with the rigid drill targeting device 1104. FIG. 19 shows the final position of guide pin 504.

Figure 20:
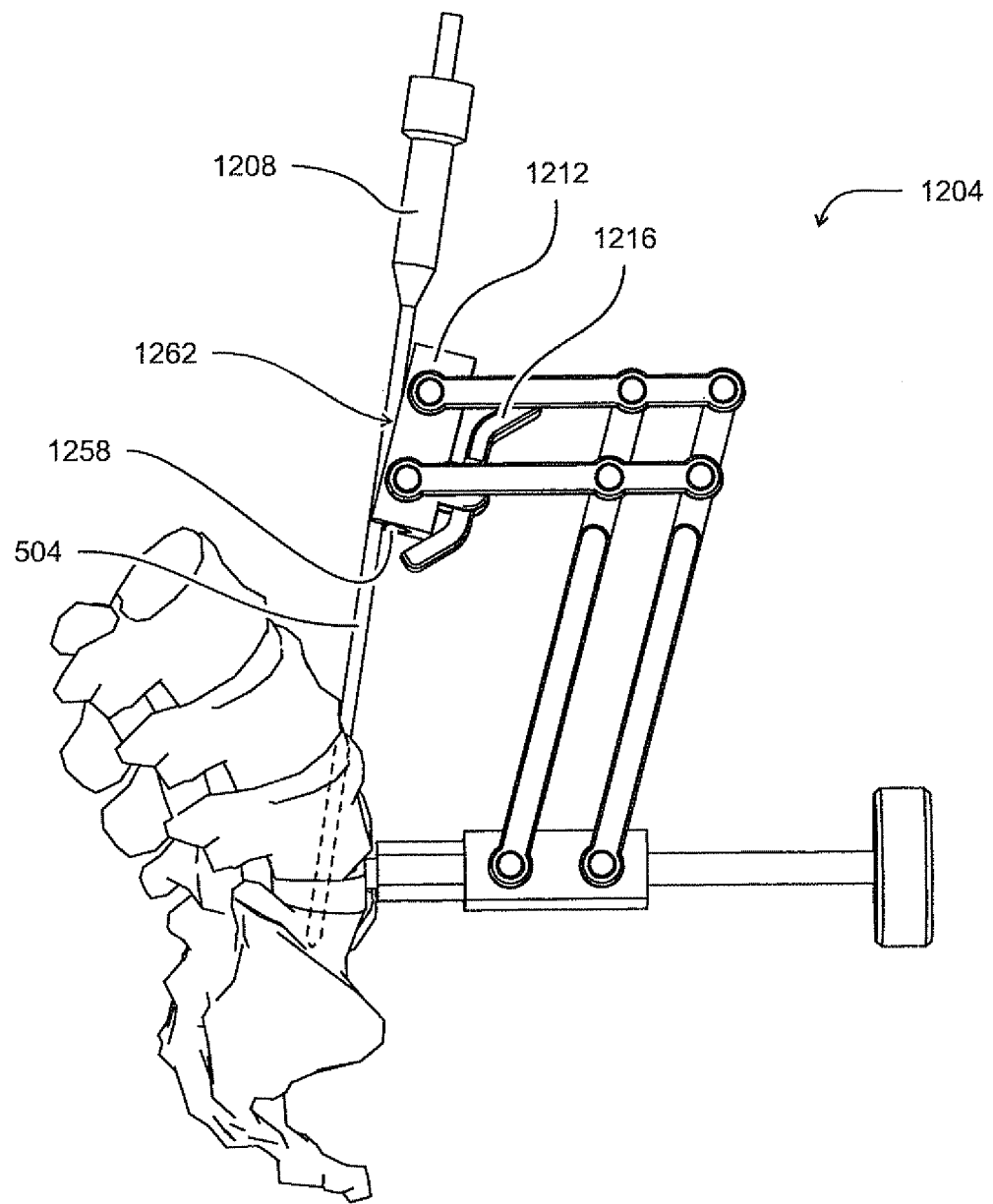
FIG. 20 shows an example removal of the articulating drill targeting device of FIGS. 17E-17H.

FIG. 20 shows removing the articulating drill targeting device 1204 as described in connection at least with FIGS. 12D, 12F, and 12G. The rigid drill targeting device 1104 is removed from guide pin 504 in a similar fashion. Thumbscrew 1118 (e.g. FIG. 11A) is loosened. Drill guide 1108 is slid up and off from the guide pin 504 and the rigid drill targeting device 1104 is rotated back and off from the guide pin 504 in a manner identical to the articulating drill targeting device 1204. The drill target 1116 is then disengaged from fixation screwhole 914 and extracted out of the utility screwhole 920.

Figure 21:
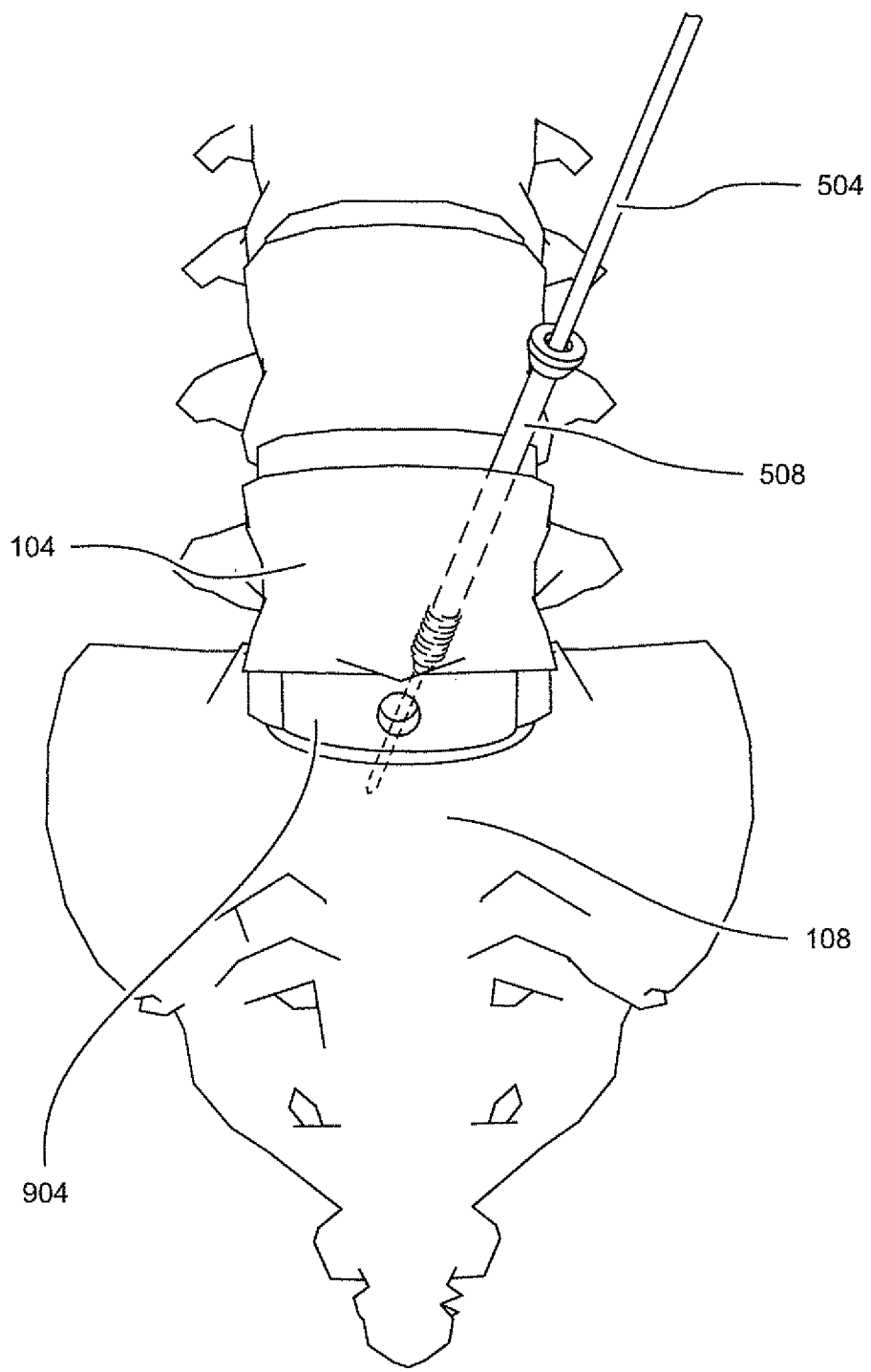
FIG. 21 shows an example insertion of a fixation screw.

FIG. 21 shows screwing in the fixation screw 508. Depending on surgeon preference, drilling over guide pin 504 using cannulated drill 1270 (e.g. FIG. 12I) may first be performed. Fixation screw 508 is then inserted over guide pin 504 using the cannulated flexible screwdriver 1274 (e.g. FIG. 12I). If the surgeon prefers, these steps can be performed through the flexible screw insertion tissue protector 1266 as described in connection at least with FIG. 12I.

Figure 22:
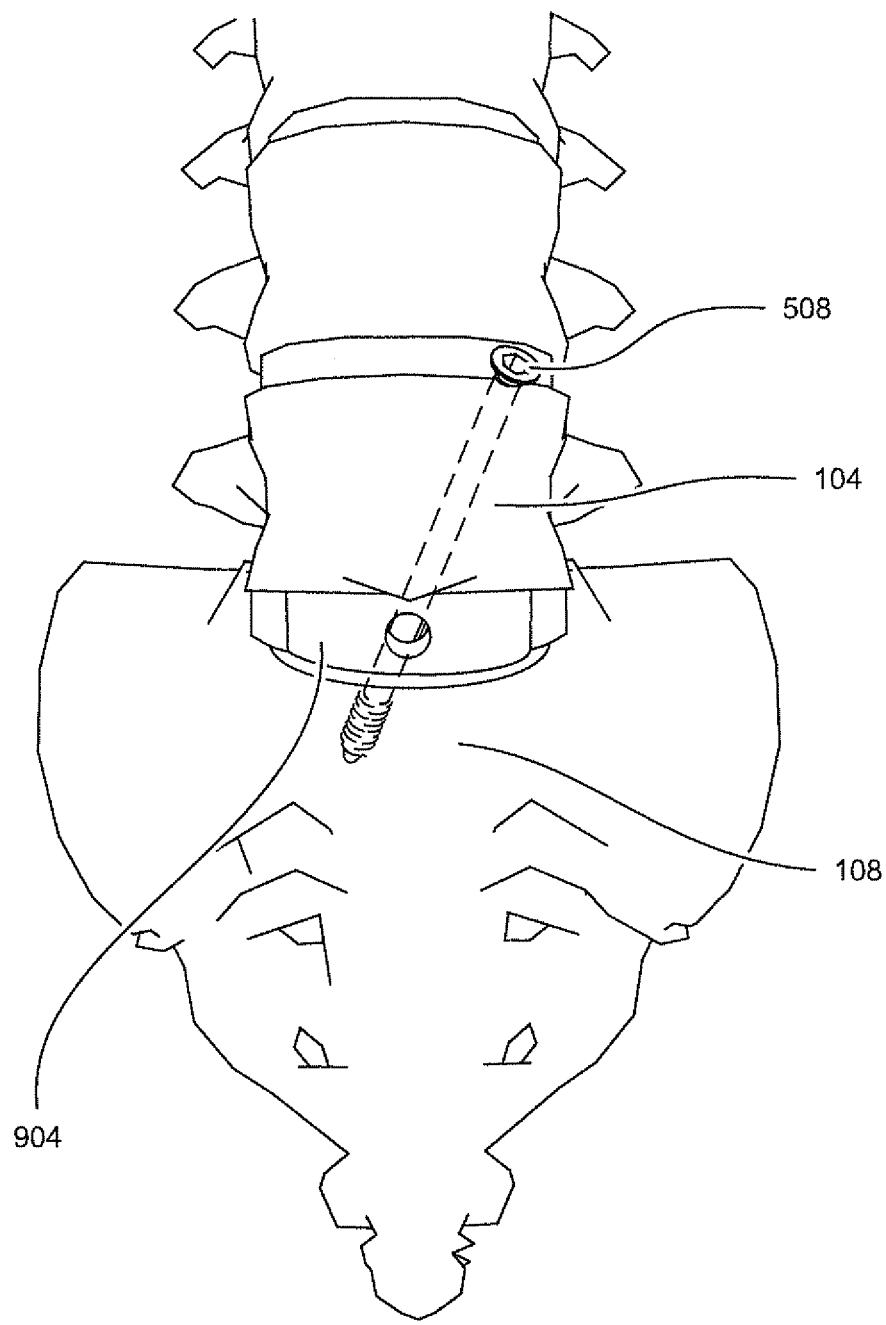
FIG. 22 shows an example of the fixation screw of FIG. 21 being in a final position.

FIG. 22 shows extracting the guide pin 504 leaving the fixation screw 508 in its final position, thereby firmly fixing modified fusion cage 904 in position between the L5 backbone 104 and the S1 backbone 108.

Figure 23:
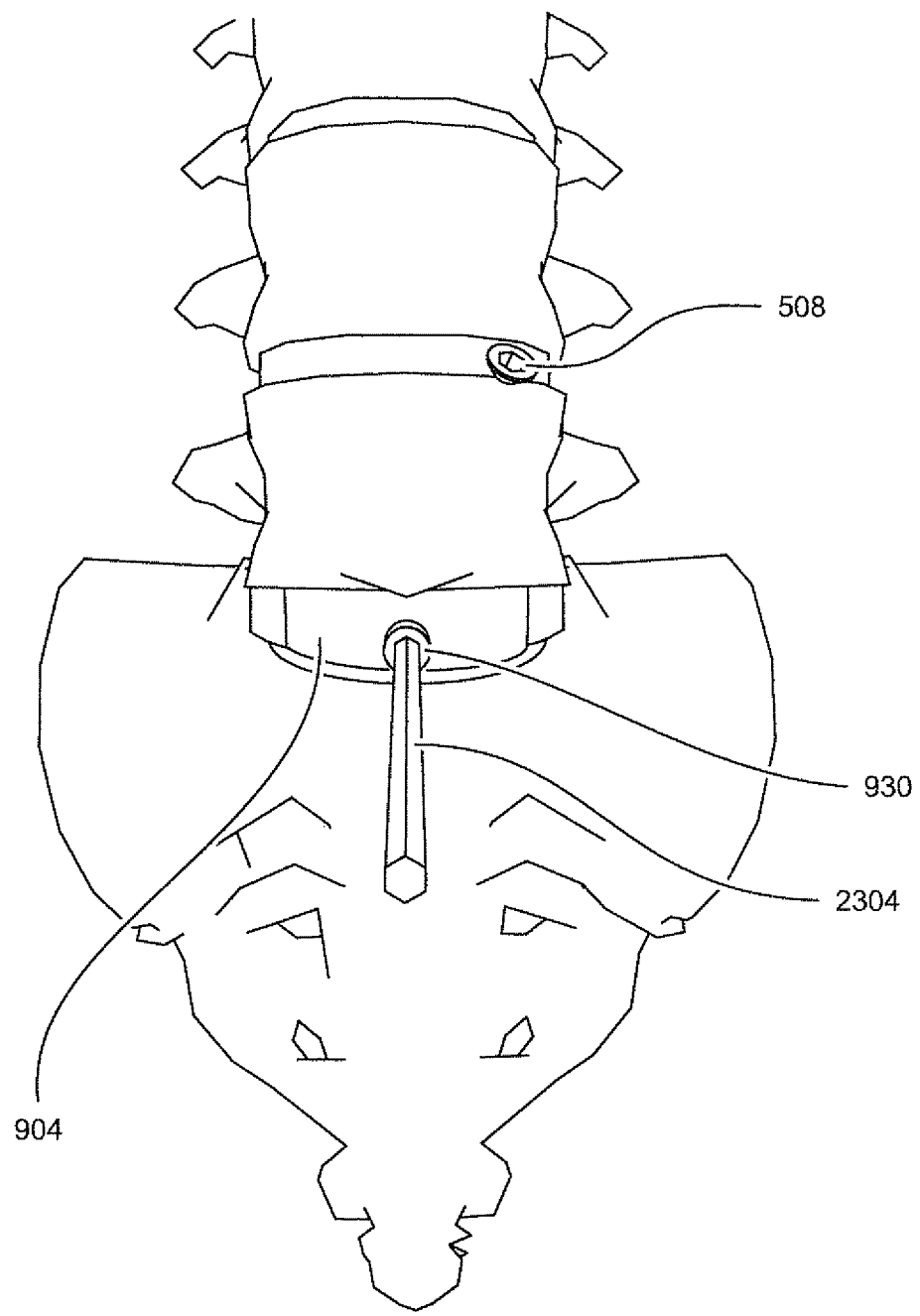
FIG. 23 shows an example of the fixation screw of FIGS. 21-22 being locked.

FIG. 23 shows locking the fixation screw 508 to the modified fusion cage 904 by inserting locking screw 930 into utility screwhole 920 using for example a hex screwdriver 2304.

Additional Information

The embodiments disclosed herein allow the accurate visual identification of a variable entry point into bone, the accurate mechanical identification of a fixed screwhole in a fusion cage positioned in a disc space, and the accurate control of the drill path between these two points.

Repeated X-rays are not required to adjust trajectory as the guide pin is advanced. Radiation exposure to the patient and to the surgeon is thereby reduced.

The continuous presence of an X-ray machine in the operative field is not required and therefore the surgeon's view of and access to the operative site during a critical phase of the surgery are not blocked.

Repeated adjustments of the trajectory during drilling are not required thus avoiding deflection of the guide pin down a misdirected drill path or drilling at a new entry point.

The ability to safely and accurately achieve bone fixation by placing the screw through the cage in this fashion avoids alternative fixation methods. These methods may involve making a separate incision. They may involve closing the present incision and turning the patient over to make a separate incision on the opposite side of the body. Avoiding the requirement to make a separate incision or to turn the patient over shortens the operative time for the patient and reduces the surgical insult to the patient.

A fusion cage may displace when a patient is turned over in the operating room in order to put alternative fixation in through a separate incision on the opposite side of the body. Fixing the cage with the screw in this fashion at the same time and through the same incision as the cage is placed avoids this risk of cage displacement.

The prominence of large implants used as an alternate fixation method on the surface of the bone, which can irritate or injure adjacent structures, is avoided.

A smaller diameter screwhole in the fusion cage results in a reduced distance the cage can displace before being stopped by the side of the screwhole contacting the screw.

A smaller diameter screwhole facilitates the design of a mechanism to lock the cage to the screw.

Having a fusion cage with a fenestration dedicated to the screw only and made as small in diameter as the screw, avoids partial cage displacement, damage to the graft material by the screw, and maximizes the area of remaining fenestrations for graft. This lessens the risk of a loose cage which can lead to failure of fusion.

Passing the screw through such a small screwhole is only feasible utilizing the drill targeting device.

The hourglass shape of the screwhole in modified cage 904 gives the smallest diameter fixed screwhole that will allow screw entry from multiple directions.

Connecting the utility screwhole to the center of the fixation screwhole allows the center of the screwhole to be accessed by the target of a rigid drill targeting device. The targeting device can then rotate on this center point allowing the guide pin to approach from varied trajectories yet still direct the guide pin through the center of the screwhole. This feature allows the use of a locking screw which decreases the risk of the fixation screw migrating in or backing out. It further diminishes any movement between the cage and fixation screw.

The modified cage 1004 with the tilting, bearing, or snap ring fixation screwhole allows the screwhole to be the same diameter as the fixation screw while still permitting screw entry from multiple trajectories. Having the fixation screwhole the same diameter as the fixation screw prevents any undesired movement between the screw and cage. The snap ring can act as a locking mechanism on the fixation screw so the separate locking screw is not necessarily required. The metal tilting, bearing, or snap ring can protect the fusion cage, which is usually made of plastic, from damage by the guide pin as it passes through the screwhole. If the guide pin is slightly off center, it can deflect off the metal bearing or snap ring rather than dig into the side wall of a plastic cage with the fixed hole.

Unlike previous cages, use of the x-ray machine is not required. Radiation exposure to the patient and operating room personnel is reduced. Surgeon and assistants having to move out of the way of the x-ray machine at the critical point in the operation is avoided. The guide pin can be placed on the first pass. Multiple trajectory changes are avoided. The operation is performed faster. Not bringing the x-ray machine into the operative field and performing the operation faster both decrease the risk of wound contamination and infection, decrease blood loss, and decrease expense of operating room time. No exceptional hand-eye skills are necessary on the surgeon's part in order to drill the guide pin through the cage.

The drill targeting device makes it possible to pass the guide pin on the first attempt case after case. No trajectory adjustments are required. Deflection of the guide pin down a misdirected drill path is avoided. Restarting pin entry at a new entry site to avoid an old drill path is not required. The rigid drill targeting device allows the surgeon to select from multiple possible entry points. He can select the entry point that best avoids important adjacent anatomical structures and at the same time pass the pin through the center of a minimum diameter screwhole.

The articulated drill targeting device has the advantages of the rigid. In addition, the articulated has a wider unrestricted range of movement in the font-to-back direction. Since it is not necessary to pass a narrow targeting arm into the center of the cage, the risk of a bent target arm misdirecting the guide pin is avoided. Since it is mounted to the insertion handle which is screwed into the cage, the connection of the targeting device to the cage is secure. The risk of the targeting device disengaging from the cage and misdirecting a screw is avoided. The ratcheting locking lever on the drill guide allows the surgeon to push the drill guide down against the bone with one hand without having to depress the locking lever. The drill guide is then firmly clamped onto the bone with the cage in the disc space on one end and the drill guide engaging the bone on the other. The locking lever will prevents the targeting device from coming unclamped by the drill guide inadvertently backing up.

Incorporating a guide pin exit slot allows the targeting device to be removed from the pin without sliding it up and off of the pin. At times it is necessary for the guide pin to enter the abdominal wall through a small incision separate from the larger incision in which the cage is placed into the disc and through which the targeting device is attached to the cage. The targeting device cannot be slid up and off of the pin in this circumstance. The guide pin exit slot makes it possible for the guide pin to be placed through this small separate incision yet still makes it possible for the surgeon to remove the targeting device from the pin.

The alignment pin on the side of the drill guide controls rotation of the drill guide in the guide block and keeps the serrations on the drill guide oriented facing the locking lever.

Having depth markings and numbers on the drill guide enables the targeting device to double as a measuring caliper. The depth to which the guide pin should be inserted and the length of the fixation screw that is required can be determined using this feature avoiding the necessity of doing it with an x-ray as has been historically required.

The ability to pass a screw through a fusion cage through the same incision on the front of the abdomen avoids having to make a separate incision on the back of the patient to insert other types of fixation screws that join the bones together. Fewer incisions mean shorter operative times, less blood loss, less risk of infection. Injury to the back muscles that occurs with this separate incision on the back is avoided. Displacement of the cage occurring when the patient is being turned over to put screws in from the back is avoided.

It is anticipated that various changes may be made in the arrangement and operation of the system of the present invention without departing from the spirit and scope of the invention, as defined by the following claims.

What is claimed is:
1. A spinal fusion system, comprising:
 a spinal fusion cage having:
  a front, back, left side, right side, top, and bottom,
  a centrally-located fixation screwhole extending from top to bottom of said cage, a solid portion of said cage having said fixation screwhole located therein,
a non-solid portion of said cage having bone graft fenestrations extending from top to bottom of said cage,
said fixation screwhole having:
  an hourglass shape with a waist,
  a minimum diameter of said fixation screwhole at said waist of said hourglass shape, and
a bone fixation screw having:
  a head, a uniform cylindrical shaft, a threaded portion, and a tapered tip,
wherein said fixation screw is positionable in said hourglass-shaped fixation screwhole:
  at an angle variable side-to-side relative to said fusion cage, and
  at an angle variable front-to-back relative to said fusion cage, up to a maximum angle,
wherein said hourglass-shaped fixation screwhole minimum diameter is defined by:
  the diameter of the cylindrical shaft of said fixation screw, and
  the maximum angle at which said fixation screw is positionable in said hourglass-shaped fixation screwhole.

2. The system of claim 1 wherein the spinal fusion cage incorporates a utility screwhole connected to the fixation screwhole.

3. The system of claim 2 further comprising a locking screw that can be inserted into said utility screwhole of said fusion cage to rigidly engage said fixation screw, whereby backing out of said fixation screw is prevented and whereby movement between said fixation screwhole and said fixation screw is eliminated.

4. The apparatus of claim 2 wherein the fixation screw is located through the fixation screwhole at a selected angle variable side-to-side and front-to-back without x-ray or other imaging guidance, utilizing a rigid drill targeting device having a drill target mounted on a drill arm, wherein the drill target fits through the utility screwhole.

5. The apparatus of claim 1 wherein the fixation screw is placed through the fixation screwhole of said spinal fusion cage at a selected angle variable side-to-side and front-to-back without x-ray or other imaging guidance utilizing an articulating drill targeting device mounted on a rod that is screwed into a utility screwhole in said spinal fusion cage said articulating drill targeting device allowing adjustment of a trajectory of the fixation screw side-to-side and front-to-back, wherein said articulating drill targeting device comprises articulating linkages in the form of two interconnected parallelograms.

6. A spinal fusion system, comprising:
  a spinal fusion cage, said cage having a front, back, left side, right side, top, and bottom,
  said cage having a centrally-located fixation screwhole extending from top to bottom of said cage, wherein a fixation screw fits through said fixation screwhole at an angle variable side-to-side and front-to-back,
  said fixation screwhole configured to maintain contact with a shaft of said fixation screw at said angle variable side-to-side and front-to-back,
  where said fixation screw is placed through said fixation screwhole at said angle variable side-to-side and front-to-back without x-ray or other imaging guidance;
  said fixation screwhole having a snap ring recess to accommodate a tilting snap ring and
  an anti-spin recess to accommodate an anti-spin tab on said tilting snap ring;
  a snap ring having a circular outer surface with a projecting anti-spin tab and a circular central hole, said circular outer surface complementary to a sidewall of said snap ring recess, said circular central hole having a smooth uniform cylindrical surface complementary to the shaft of said fixation screw, said anti-spin tab fitting into said anti-spin recess, said snap ring being free to tilt side-to-side and front-to-back in said fixation screwhole, where spinning of said snap ring is prevented by said anti-spin tab engaging said anti-spin recess;
  said bone fixation screw having a tapered tip, a threaded end, and a smooth uniform cylindrical shaft, said tapered tip and said tilting snap ring permitting entry of said screw into said central hole of said snap ring from variable angles, said tapered tip tilting said snap ring orthogonal to said fixation screw, said tapered tip expanding said snap ring thereby engaging said circular outer surface of said snap ring with the side walls of said fixation screwhole, said cylindrical shaft of said fixation screw permitting advancement of said fixation screw while maintaining expansion and engagement of said snap ring with the sidewalls of said fixation screwhole, wherein spinning of said snap ring is prevented by the engagement of said anti-spin tab of said snap ring in said anti-spin recess of said fixation screwhole,
  wherein said spinal fusion cage is prevented from migrating side-to-side or front-to-back in relation to the shaft of said fixation screw and whereby said fixation screw is inhibited from backing out of said fixation screwhole by a friction fit between the shaft of said fixation screw and said tilting snap ring.

7. The system of claim 6 wherein the spinal fusion cage incorporates a utility screwhole connected to the fixation screwhole.

8. The system of claim 7 further comprising a locking screw inserted into said utility screwhole of said fusion cage to rigidly engage said fixation screw, whereby hacking out of said fixation screw is prevented.

9. The system of claim 7 wherein the fixation screw is placed through the fixation screwhole of said spinal fusion cage at a selected angle variable side-to-side and front-to-back without x-ray or other imaging guidance utilizing a rigid drill targeting device having a drill target mounted on a drill arm, wherein the drill target fits through the utility screwhole.

10. The system of claim 6 wherein the fixation screw is placed through the fixation screwhole of said spinal fusion cage at a selected angle variable side-to-side and front-to-bark without x-ray or other imaging guidance utilizing an articulating drill targeting device mounted on a rod that is screwed into the utility screwhole in said spinal fusion cage, said articulating drill targeting device allowing adjustment of a trajectory of the fixation screw side-to-side and front-to-back, wherein said articulating drill targeting device comprises articulating linkages in the form of two interconnected parallelograms.

* * * * *